US007462352B2

(12) United States Patent
Hansen et al.

(10) Patent No.: US 7,462,352 B2
(45) Date of Patent: Dec. 9, 2008

(54) METHODS OF TREATNG B-CELL DISEASES USING HUMANIZED ANTI-CD19 ANTIBODIES

(75) Inventors: Hans J. Hansen, Picayune, MS (US); Zhengxing Qu, Warren, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 11/445,410

(22) Filed: Jun. 1, 2006

(65) Prior Publication Data

US 2006/0257398 A1    Nov. 16, 2006

Related U.S. Application Data

(62) Division of application No. 10/903,858, filed on Aug. 2, 2004, now Pat. No. 7,109,304.

(60) Provisional application No. 60/491,282, filed on Jul. 31, 2003.

(51) Int. Cl.
*A61K 51/00* (2006.01)
*A61K 49/00* (2006.01)
*A61K 39/395* (2006.01)
*C07K 17/00* (2006.01)

(52) U.S. Cl. .................. 424/130.1; 424/9.1; 424/133.1; 424/134.1; 424/136.1; 424/143.1; 424/152.1; 424/153.1; 424/174.1

(58) Field of Classification Search ........................ None
See application file for complete search history.

(56) References Cited

U.S. PATENT DOCUMENTS

| 5,798,554 | A  | 8/1998  | Grimaldi et al. |
| 6,183,744 | B1 | 2/2001  | Goldenberg |
| 6,187,287 | B1 | 2/2001  | Leung et al. |
| 6,306,393 | B1 | 10/2001 | Goldenberg |
| 6,653,104 | B2 | 11/2003 | Goldenberg |
| 2003/0133930 | A1 | 7/2003 | Goldenberg |

FOREIGN PATENT DOCUMENTS

| WO | WO 96/36360 | * | 11/1996 |
| WO | 0074718 A1 | | 12/2000 |

OTHER PUBLICATIONS

Bataille et al. Haematologica Sep. 2006;91(9):1234-1240.*

Matsushita et al. American Journal of Pathology 2006, 168;3:812-821.*

Cochlovius, Bjorn, et al., "Treatment of Human B Cell Lymphoma Xenografts with a CD3 x CD19 Diabody and T Cells" the Journal of Immunology, 2000, 165: 888-895.

EK, Onur, et al., "Treatment of Human B-Cell Precursor Leukemia in SCID Mice by Using a Combination of the anti-CD19 Immunotoxin B43-PAP with the Standard Chemotherapeutic Drugs Vincristine, Methylprednisolone, and L-Asparaginase" Leukemia and Lymphoma, vol. 31, pp. 143-149.

Ghetie, Maria-Ana, et al., "Homodimers but not monomers of Rituxan (chimeric anti-CD20) induce apoptosis in human B-lymphoma cells and synergize with a chemotherapeutic agent and an immunotoxin" Blood. 2001;97:1392-1398).

Ghetie, Maria-Ana, et al., "Evalution of Ricin A Chain-containing Immunotoxins Directed against CD19 and CD22 Antigens on Normal and Malignant Human B-Cells as Potential Reagents for in Vivo therapy" Cancer Research 48, 2610-2617, 1988.

Ghetie, Maria-Ana, et al., "Homodimerization of tumor-reactive monoclonal antibodies markedly increases their ability to induce growth arrest or apoptosis of tumor cells" Proc. Natl. Acad. Sci. USA vol. 94, pp. 7509-7514, Jul. 1997.

Ghetie, Maria-Ana, et al., "The Antitumor Activity of an Anti-CD22 Immunotoxin in SCID Mice with Disseminated Daudi Lymphoma is Enhanced by Either an anti-CD19 Antibody or an Anti-CD19 Immunotoxin" Blood, vol. 80, No. 9 (Nov. 1), 1992: pp. 2315-2320.

Hekman, A., et al., "Initial experience with treatment of human B cell lymphoma with anti-CD19 monoclonal antibody" Cancer Immunol Immunother (1991) 32: 364-372.

Ma, D., et al., "Radioimmunotherapy for model B cell malignancies using 90Y-labeled anti-CD19 and anti-CD20 monoclonal antibodies" Leukemia (2002) 16, 60-66.

Mitchell, Paul, et al., "Targeting Primary Human Ph+ B-Cell Precursor Leukemia-Engrafted SCID Mice Using Radiolabeled Anti-CD19 Monoclonal Antibodies" J Nucl Med 2003; 44:1105-1112.

Majolino, Patti, C., "High-dose cyclophosphamide, etoposide and BCNU (CVB) with autologous stem cell rescue in malignant lymphomas" European Journal of Haematology 1993: 51: 18-24.

(Continued)

*Primary Examiner*—Maher M. Haddad
*Assistant Examiner*—Chun Dahle
(74) *Attorney, Agent, or Firm*—Richard A. Nakashima

(57) ABSTRACT

The present invention provides humanized, chimeric and human anti-CD19 antibodies, anti-CD19 antibody fusion proteins, and fragments thereof that bind to a human B cell marker. Such antibodies, fusion proteins and fragments thereof are useful for the treatment and diagnosis of various B-cell disorders, including B-cell malignancies and autoimmune diseases.

21 Claims, 9 Drawing Sheets

OTHER PUBLICATIONS

Roguska, Michael A., et al., "Humanization of murine monoclonal antibodies through variable domain resurfacing" Proc. Natl. Acad. Sci. USA vol. 91, pp. 969-973, Feb. 1994.

Rowland, A. J., et al., "Preclinical invesigation of the antitumour effects of anti-CD19-idarubicin immunoconjugates" Cancer Immunol Immunother (1993) 37: 195-202.

Shan, Daming, et al., "Signaling events involved in anti-CD20-induced apoptosis of malignant human B cells" Cancer Immunol Immunother (2000) 48:673-683.

Stone, Marvin J., et al., "A phase I Study of Bolus Versus Continuous Infusion of the anti-CD19 Immunotoxin, IgG-HD37-dgA, in Patients with B-Cell Lymphoma" Blood, vol. 88, No. 4 (Aug. 15, 1996, pp. 1188-1197.

Uckun, Fatih M., et al., "Treatment of Therapy-Refractory B-Lineage Acute Lymphoblastic Leukemia with an Apoptosis-inducing CD19-directed Tyrosine Kinase Inhibitor" Clincial Cancer Research vol. 5, 3906-3913, Dec. 1999.

Uckun, Fatih M., et al., "Detailed Studies on Expression and Function of CD19 Surface Determinant by Using B43 Monoclonal Antibody and the Potential of Anti-CD19 Immunotoxins" Blood, vol. 71, No. 1 (Jan. 1988; pp. 13-29.

Uckun, Fatih M., "Effective Immunochemotherapy of CALLA +Cu+ Human Pre-B Acute Lymphoblastic Leukemia in Mice with Severe Combined Immunodeficency Using B43 (anti-CD19) Pokeweed Antiviral Protein Immunotoxin Plus Cyclophosphamide" Blood, vol. 79, No. 12 (Jun. 15, 1992; pp. 3116-3129.

Zola, H., et al., "Preparation and characterization of a chimeric CD19 monoclonal antibody" Immunology and Cell Biology (1991) 69, 411-422.

Pietersz, Geoffrey A., et al., "In vitro and in vivo antitumour activity of a chimeric anti-CD19 antibody" Cancer Immunol Immunother (1995) 41: 53-60.

Roguska, Michael A., et al., "A comparison of two murine monoclonal antibodies humanized by CDR-grafting and variable domain resurfacing" Protein Engineering vol. 9, No. 10, pp. 895-904, 1996.

* cited by examiner

```
GACATCCAGCTGACCCAGTCTCCAGCTCTCCTTGGCTGTGTCTCTAGGGCAGAGGGCCACCATCTCCTGCAAGGCCAGCCAAAGTGTTGAT
  1                                        10                                        20                              27 A B C
  D   I   Q   L   T   Q   S   P   A   S   L   A   V   S   L   G   Q   R   A   T   I   S   C   K   A   S   Q   S   V   D

TATGATGGTGATAGTTATTTGAACTGGTACCAACAGATTCCAGGACAGCCACCCAAACTCCTCATCTATGATGCATCCAATCTAGTTTCT
  D                           30                                        40                                        50
  Y   D   G   D   S   Y   L   N   W   Y   Q   Q   I   P   G   Q   P   P   K   L   L   I   Y   D   A   S   N   L   V   S
      CDR1                                                                                          CDR2

GGCATCCCACCCAGTTTAGTGGCAGTGGGTCTGGGACAGACTTCACCCTCAACATCCATCCTGTGGAGAAGGTGGATGCTGCAACCTAT
                    60                                        70                                        80
  G   I   P   P   R   F   S   G   S   G   S   G   T   D   F   T   L   N   I   H   P   V   E   K   V   D   A   A   T   Y

CACTGTCAGCAAAGTACTGAAGATCCGTGGACGTTCGGTGGAGGGACCAAGCTGGAGATCAAACGT
                              90                                      100                       108
  H   C   Q   Q   S   T   E   D   P   W   T   F   G   G   G   T   K   L   E   I   K   R
              CDR3
```

90

180

270

336

Figure 1A. Nucleotide and Amino Acid Sequences of the chimeric anti-CD19 Ab, cA19, $V_K$

```
CAGGTCCAACTGCAGGAGTCTGGGGCTGAGCTGGTGAGGCCTGGGTCCTCAGTGAAGATTTCCTGCAAGGCTTCTGGTTATGCATTCAGT      90
  1                                               10                                      20                                      30
  Q   V   Q   L   Q   E   S   G   A   E   L   V   R   P   G   S   S   V   K   I   S   C   K   A   S   G   Y   A   F   S

AGCTACTGGATGAACTGGGTGAAGCAGAGGCCTGGACAGGGTCTTGAGTGGATTGGACAGATTTGGCCTGGAGATGGTGATACTAACTAC     180
                                      40                                      50     52 A                                 
  S   Y   W   M   N   W   V   K   Q   R   P   G   Q   G   L   E   W   I   G   Q   I   W   P   G   D   G   D   T   N   Y
      CDR1                                                                    CDR2

AATGGAAAGTTCAAGGGTAAAGCCACTCTGACTGCCGACGAATCCTCCAGCACAGCCTACATGCAACTCAGCAGCCTACGATCTGAGGAC     270
 60                                  70                                  80     82 A B C
  N   G   K   F   K   G   K   A   T   L   T   A   D   E   S   S   S   T   A   Y   M   Q   L   S   S   L   R   S   E   D

TCTGCGGTCTATTCTTGTGCAAGACGGGAGACTACGACGGTAGGCCGTTATTACTATGCTATGGACTACTGGGGCCAAGGGACCACGGTC     336
                              90                  100 A B C D E F G
  S   A   V   Y   S   C   A   R   R   E   T   T   T   V   G   R   Y   Y   Y   A   M   D   Y   W   G   Q   G   T   T   V
                                                      CDR3

ACCGTCTCCTCA                                                                                   336
110        113
  T   V   S   S
```

Figure 1B. Nucleotide and Amino Acid Sequences of cA19 V$_H$

```
         1                    10                 20              27 A B C D    30
REIVk    DIQMTQSPSSLSASVGDRVTITC QASQ----DIIKYLNWY
cA19Vk   ...L.....A..AV.L.Q.A..S. K...SVDY.GDS....
hA19Vk   ...L.................... K...SVDY.GDS....

40                    50                60                  70
REIVk    QQTPGKAPKLLIY EANSLQA GVPSRFSGSGSGTDYTFTIS
cA19Vk   ...I..QP..... D.SN.VS .I.P............F.LN.H
hA19Vk   ...I......... D.SN.VS .I.P.................

80                    90                100
REIVk    SLQPEDIATYYC QQYQSLPYT FGQGTKLQITR
cA19Vk   PVEKV.A...H. ....STED.W ...G....K..
hA19Vk   ............H ....STED.W ...G....K..
```

Figure 3A. Amino Acid Sequences of REI $V_K$, cA19 $V_K$, and hA19 $V_K$

```
               1                    10                    20                      30                   40
EUVH      QVQLVQSGAEVKKPGSSVKVSCKASGGTFSS YWLH WVRQA
cA19VH    ....QE....LVR........I........YA...·MN···K·R
hA19VH    .....Q...............I........YA...·MN·····R 50 52 A                       60                    70
EUVH      PGQGLEWMG GIVPMFGPPNYAQKFQG RATITADESTNTAY
cA19VH    .........I..Q·W·GD·DT···NG··K···········L·····SS·
hA19VH    .........I..Q·W·GD·DT···NG··K···················SS·

80 82 A B C              90                 100 A B C D E F G
EUVH      MELSSLRSEDTAFYFCAG GYGIYS------PE
cA19VH    ·Q·············S·V·S··RRETTTVGRYYYAMDY
hA19VH    ................S·····RRETTTVGRYYYAMDY 103               110
NEWMVH    WGQGSLVTVSS
cA19VH    ....TT.....
hA19VH    ....TT.....
```

Figure 3B. Amino Acid Sequences of EU V$_H$ (FR1-3), NEWM V$_H$ (FR4), cA19V$_H$, and hA19 V$_H$

```
GACATCCAGCTGACCCAGTCTCCATCATCTCTGAGCGCATCTGTTGGAGATAGGGTCACTATCACTTGTAAGGCCAGCCAAAGTGTTGAT      90
  1                    10                    20                    27 A B C D
  D   I   Q   L   T   Q   S   P   S   S   L   S   A   S   V   G   D   R   V   T   I   T   C   K   A   S   Q   S   V   D

TATGATGGTGATAGTTATTTGAACTGGTACCAGCAGATTCCAGGGAAAGCACCTAAATTGTTGATCTACGATGCTTCGAATCTAGTTTCT     180
  D              30                    40                    50
  Y   D   G   D   S   Y   L   N   W   Y   Q   Q   I   P   G   K   A   P   K   L   L   I   Y   D   A   S   N   L   V   S
      CDR1                                                                          CDR2

GGTATCCCTCCTCGATTCTCTGGCAGCGGATCTGGGACAGATTACACTTTCACCATCAGCTCTCTTCAACCAGAAGACATTGCAACATAT     270
                      60                    70                    80
  G   I   P   P   R   F   S   G   S   G   S   G   T   D   Y   T   F   T   I   S   S   L   Q   P   E   D   I   A   T   Y

CACTGTCAGCAAAGTACTGAAGATCCGTGGACGTTCGGTGGAGGGACCAAGCTACAGATCAAACGT                              336
                      90                    100               108
  H   C   Q   Q   S   T   E   D   P   W   T   F   G   G   G   T   K   L   Q   I   K   R
          CDR3
```

Figure 4A. Nucleotide and Amino Acid Sequences of hA19 V$_K$

```
CAGGTCCAACTGCAGCAGTCAGGGGCTGAAGTCAAGAAACCTGGGTCATCGGTGAAGGTCTCCTGCAAGGCTTCTGGCTACGCTTTCAGT    90
 1                                     10                   20                     30
  Q  V  Q  L  Q  Q  S  G  A  E  V  K  K  P  G  S  S  V  K  V  S  C  K  A  S  G  Y  A  F  S

AGCTACTGGATGAACTGGGTGAGGCAGAGGCCTGGACAGGGTCTTGAGTGGATTGGACAGATTTGGCCTGGAGATGGTGATACTAACTAC   180
  S  Y  W  M  N           40                   50       52 A              CDR2          Y
  —————————————            W  V  R  Q  R  P  G  Q  G  L  E  W  I  G  Q  I  W  P  G  D  G  D  T  N
       CDR1

AATGGAAAGTTCAAGGGCCGCCACTATTACTGCCGACGAATCCACTAATACAGCCTACATGGAACTCAGCAGCCTACGATCTGAGGAC    270
 60                   70                   80      82 A B C
  N  G  K  F  K  G  R  A  T  I  T  A  D  E  S  T  N  T  A  Y  M  E  L  S  S  L  R  S  E  D
  ——————————————

ACAGGCGTTCTATTCTGTGCAAGACGGGAGACTACGACGGTAGGCCGTTATTACTATGCTATGGACTACTGGGGCCAAGGGACCACGGTC   336
                                          90   100 A  B  C  D  E  F  G
  T  A  F  Y  S  C  A  R  R  E  T  T  T  V  G  R  Y  Y  Y  A  M  D  Y  W  G  Q  G  T  T  V
                          ————————————————————————————————————————————————
                                                  CDR3

ACCGTCTCCTCA                                                                                 336
110       113
  T  V  S  S
```

Figure 4B. Nucleotide and Amino Acid Sequences of hA19 V$_H$

METHODS OF TREATNG B-CELL DISEASES USING HUMANIZED ANTI-CD19 ANTIBODIES

BACKGROUND OF THE INVENTION

This application is a divisional to U.S. patent application Ser. No. 10/903,858 (now issued U.S. Pat. No. 7,109,304), "Humanized Anti-CD19 Antibodies" filed on Aug. 22, 2004, which claims priority to a provisional U.S. Patent Application No. 60/491,282, filed Jul. 31, 2003, the contents of which are incorporated herein by reference in their entirety.

FIELD OF THE INVENTION

The present invention relates to anti-CD19 antibodies, particularly humanized, chimeric and human anti-CD19 antibodies, particularly monoclonal antibodies (MAbs) and fragments thereof, either naked or conjugated to at least one therapeutic and/or diagnostic agent, and methods of use thereof. In particular, the anti-CD19 antibodies of the present invention can be used for treating B cell disease such as, for example, a malignancy and/or an inflammatory disease or disorder, including an autoimmune disease. The methods and compositions of the present invention can also be used to treat a lymphoma and a leukemia, including non-Hodgkin's lymphoma, chronic lymphocytic leukemia, and acute lymphoblastic leukemia. In a preferred embodiment, the neoplastic disorder is a B-cell malignancy such as indolent forms of B-cell lymphomas, aggressive forms of B-cell lymphomas (including non-Hodgkin's lymphoma), chronic lymphatic leukemias, or acute lymphatic leukemias, or multiple myeloma.

The present invention also relates to antibody fusion proteins and fragments thereof comprising at least two anti-CD19 MAbs or fragments thereof, or at least one anti-CD19 MAb or fragment thereof and at least one second MAb or fragment thereof, other than the anti-CD19 Mab or fragment thereof. The multispecific and/or fusion proteins of the present invention can be either naked or conjugated to at least one therapeutic and/or diagnostic agent.

The humanized, chimeric and human anti-CD19 Mabs and fragments thereof, and antibody fusion proteins and fragments thereof may be administered alone, either naked or conjugated to a therapeutic or diagnostic agent, or in combination with another naked antibody, fragment or immunoconjugate. Also, naked or conjugated anti-CD 19 antibodies and fragments thereof, and antibody fusion proteins and fragments thereof may be administered in combination with at least one therapeutic agent or diagnostic agent that is not conjugated to a CD 19 antibody or fragment thereof, or fusion protein or fragment thereof.

Additionally, the present invention relates to a DNA sequence encoding a humanized, chimeric or human anti-CD19 antibody and fragment thereof, and antibody fusion protein and fragment thereof. Likewise, a vector and host cell containing the DNA sequence is also contemplated. Finally, the present invention discloses methods of making the humanized, chimeric and human anti-CD 19 antibodies and fragments thereof, and fusion proteins and fragments thereof.

BACKGROUND

The immune system of vertebrates consists of a number of organs and cell types which have evolved to accurately recognize foreign antigens, specifically bind to, and eliminate/destroy such foreign antigens. Lymphocytes, among other cell types, are critical to the immune system. Lymphocytes are divided into two major sub-populations, T cells and B cells. Although inter-dependent, T cells are largely responsible for cell-mediated immunity and B cells are largely responsible for antibody production (humoral immunity).

In humans, each B cell can produce an enormous number of antibody molecules. Such antibody production typically ceases (or substantially decreases) when a foreign antigen has been neutralized. Occasionally, however, proliferation of a particular B cell will continue unabated and may result in a cancer known as a B cell lymphoma. B-cell lymphomas, such as the B-cell subtype of non-Hodgkin's lymphoma, are significant contributors to cancer mortality. The response of B-cell malignancies to various forms of treatment is mixed. For example, in cases in which adequate clinical staging of non-Hodgkin's lymphoma is possible, field radiation therapy can provide satisfactory treatment. Still, about one-half of the patients die from the disease. Devesa et al., *J. Nat'l Cancer Inst.* 79:701 (1987).

The majority of chronic lymphocytic leukemias are of the B-cell lineage. Freedman, *Hematol. Oncol. Clin. North Am.* 4:405 (1990). This type of B-cell malignancy is the most common leukemia in the Western world. Goodman et al., *Leukemia and Lymphoma* 22: 1 (1996). The natural history of chronic lymphocytic leukemia falls into several phases. In the early phase, chronic lymphocytic leukemia is an indolent disease, characterized by the accumulation of small mature functionally-incompetent malignant B-cells having a lengthened life span. Eventually, the doubling time of the malignant B-cells decreases and patients become increasingly symptomatic. While treatment can provide symptomatic relief, the overall survival of the patients is only minimally affected. The late stages of chronic lymphocytic leukemia are characterized by significant anemia and/or thrombocytopenia. At this point, the median survival is less than two years. Foon et al., *Annals Int. Medicine* 113:525 (1990). Due to the very low rate of cellular proliferation, chronic lymphocytic leukemia is resistant to cytotoxic drug treatment.

Traditional methods of treating B-cell malignancies, including chemotherapy and radiotherapy, have limited utility due to toxic side effects. The present invention minimizes drug toxicity of normal tissues by using conjugated monoclonal antibodies and antibody fragments to selectively direct a radionuclide, toxin, RNAi molecule or other therapeutic or diagnostic agent to a tumor site. In addition, unconjugated B-cell antibodies, such as anti-CD 19, -CD20, -CD21, -CD23, -CD80 and -CD22 antibodies can be used to target certain markers on B-cell malignancies. Also, other antigens, such as HLA-DR may serve as targets for both normal and malignant B-cells, even though they are also expressed on other cell types.

B cells comprise cell surface proteins which can be utilized as markers for differentiation and identification. One such human B-cell marker is a CD19 antigen and is found on mature B cells but not on plasma cells. CD19 is expressed during early pre-B cell development and remains until plasma cell differentiation. CD19 is expressed on both normal B cells and malignant B cells whose abnormal growth can lead to B-cell lymphomas. For example, CD19 is expressed on B-cell lineage malignancies, including, but not limited to non-Hodgkin's lymphoma, chronic lymphocytic leukaemia, and acute lymphoblastic leukaemia.

A potential problem with using non-human monoclonal antibodies (e.g., murine monoclonal antibodies) is typically lack of human effector functionality. In other words, such antibodies may be unable to mediate complement-dependent lysis or lyse human target cells through antibody-dependent cellular toxicity or Fc-receptor mediated phagocytosis. Furthermore, non-human monoclonal antibodies can be recognized by the human host as a foreign protein and, therefore, repeated injections of such foreign antibodies can lead to the induction of immune responses leading to harmful hypersensitivity reactions. For murine-based monoclonal antibodies, this is often referred to as a Human Anti-Mouse Antibody (HAMA) response.

The use of chimeric antibodies is more preferred because they do not elicit as strong a HAMA response as murine antibodies. Chimeric antibodies are antibodies which comprise portions from two or more different species. For example, Liu, A. Y. et al, "Production of a Mouse-Human Chimeric Monoclonal Antibody to CD20 with Potent Fc-Dependent Biologic Activity" *J. Immun.* 139/10:3521-3526 (1987), describe a mouse/human chimeric antibody directed against the CD20 antigen. See also, PCT Publication No. WO 88/04936. However, no information is provided as to the ability, efficacy or practicality of using such chimeric antibodies for the treatment of B cell disorders in the reference. It is noted that in vitro functional assays (e.g., complement-dependent lysis (CDC); antibody dependent cellular cytotoxicity (ADCC), etc.) cannot inherently predict the in vivo capability of a chimeric antibody to destroy or deplete target cells expressing the specific antigen. See, for example, Robinson, R. D. et al., "Chimeric mouse-human anti-carcinoma antibodies that mediate different anti-tumor cell biological activities," *Hum. Antibod. Hybridomas* 2:84-93 (1991) (chimeric mouse-human antibody having undetectable ADCC activity). Therefore, the potential therapeutic efficacy of a chimeric antibody can only truly be assessed by in vivo experimentation, preferably in the species of interest for the specific therapy.

One approach that has improved the ability of murine monoclonal antibodies to be effective in the treatment of B-cell disorders has been to conjugate a radioactive label or chemotherapeutic agent to the antibody, such that the label or agent is localized at the tumor site. For example, studies indicate that $^{90}$Y labeled anti-CD19 antibodies can be used to reduce lymphoma in mice (McDevitt et al., *Leukemia* 16:60 (2002>>, anti-CD19 antibodies conjugated to idarubicin result in tumor regression in an experimental model (Rowland et al., *Cancer Immunol. Immunother.,* 37:195 (1993)), and $^{125}$I and $^{111}$In radiolabeled CD19 is specifically taken up in tumor bearing organs (Mitchell et al., *J. Nucl. Med.,* 44: 1105 (2003)). Combination therapy with an anti-CD19 antibody is also described in Ek et al., *Leuk. Lymphoma* 31: 143 (1998) and Uckum et al., *Blood,* 79:3116 (1992). Treatment of human B cell lymphoma with with an anti-CD19 antibody and CD3×CD19 diabody is described in Hekman et al., *Cancer Immunol. Immunother.,* 32:364 (1991) and Cochlovius et al., *J. Immunol.,* 165:888 (2000), respectively.

However, these approaches have not eliminated the obstacles associated with using murine antibodies, despite the fact that many patients with lymphoma who have received prior aggressive cytotoxic chemotherapy are immune suppressed, thus having lower HAMA rates than lymphoma patients who have not been heavily pretreated.

Inflammatory diseases, including autoimmune diseases are also a class of diseases associated with B-cell disorders. Examples of autoimmune diseases include, but are not limited to acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, parnphigus vulgaris, Wegener's granulomatosis, membranous nephropathy, amyotrophic lateral sclerosis, tabes dorsalis, giant cell arteritis/polymyalgia, perniciousanemia, rapidly progressive glomerulonephritis, psoriasis, and fibrosing alveolitis. The most common treatments are corticosteroids and cytotoxic drugs, which can be very toxic. These drugs also suppress the entire immune system, can result in serious infection, and have adverse affects on the bone marrow, liver and kidneys. Other therapeutics that have been used to treat Class III autoimmune diseases to date have been directed against T-cells and macrophages. There is a need for more effective methods of treating autoimmune diseases, particularly Class III autoimmune diseases.

To address the many issues related to B-cell disorders and their treatment, the present invention provides humanized, chimeric and human anti-CD19 monoclonal antibodies and fragments thereof, and antibody fusion proteins and fragments thereof for the treatment of B cell lymphomas and leukemias and autoimmune disorders in humans and other mammals without the adverse responses associated with using murine antibodies. The antibodies, fusion proteins and fragments thereof of the present invention can be used alone, conjugated to at least one diagnostic and/or therapeutic agent or in combination with other treatment modalities.

SUMMARY OF THE INVENTION

Accordingly, the present invention provides humanized, chimeric and human anti-CD19 antibodies that bind to a human B cell marker, referred to as CD19, which is useful for the treatment and diagnosis of B-cell disorders, such as B-cell malignancies and autoimmune diseases.

The present invention further provides methods of treatment of mammalian subjects, such as humans or domestic animals, with one or more humanized, chimeric or human CD19 antibodies, alone, as an antibody fusion protein, as a therapeutic conjugate alone or as part of an antibody fusion protein, in combination, or as a multimodal therapy, with other antibodies, other therapeutic agents or immunomodulators or as an immunoconjugate linked to at least one therapeutic agent, therapeutic radionuclide or immunomodulator. These humanized, chimeric and human CD19 antibodies can also be used as a diagnostic imaging agent alone, in combination with other diagnostic imaging agents, and/or in conjunction with therapeutic applications.

The present invention additionally is directed to anti-CD19 MAbs or fragments thereof that contain specific murine CDRs or a combination of murine CDRs from more than one murine or chimeric anti-CD19 MAb that have specificity for CD19. These MAbs can be humanized, chimeric or human anti-CD19 MAbs.

The present invention is also directed to antibody fusion proteins comprising at least two anti-CD19 MAbs or fragments thereof or a first MAb comprising an anti-CD19 MAb or fragment thereof and a second MAb.

The present invention is further directed to a therapeutic or diagnostic conjugate of the anti-CD19 MAbs or fragments thereof and antibody fusion proteins of the anti-CD19 MAbs or other MAbs or fragments thereof bound to at least one therapeutic agent and/or at least one diagnostic agent. Antibody fusion proteins with multiple therapeutic agents of the same or different type are also contemplated in the present invention.

The present invention is additionally directed to a method of using the anti-CD19 MAbs or fragments thereof or antibody fusion proteins thereof or fragments thereof for therapy, either alone, in combination with each other, naked, conjugated to one or more therapeutic agents or each administered in combination with one or more therapeutic agents.

The present invention further is directed to a method of using the anti-CD19 MAbs or fragments thereof or antibody fusion proteins thereof or fragments thereof as a diagnostic bound to one or more diagnostic agents.

BRIEF DESCRIPTION OF THE FIGURES

FIG. 1 discloses the $V_K$, the variable light chain, and the VH, the variable heavy chain, sequences of cA19, a chimeric anti-CD 19 antibody. The CDR region sequences are shown in bold and underlined. The nucleotides are numbered sequentially. Kabat's Ig molecule numbering is used for amino acid residues as shown by the numbering above the amino acid residues. The amino acid residues numbered by letters are the insertion residues defined by Kabat numbering scheme. The insertion residues have the same preceding digits as that of the previous residue. For example, residues 82, 82A, 82B, and 82C in FIG. 1B are indicated as 82, A, B, and C, respectively. The light chain variable region is shown in FIG. 1A (SEQ ID NO:1 and SEQ ID NO:2) and the heavy chain variable region is shown in FIG. 1B (SEQ ID NO:3 and SEQ ID NO:4).

FIG. 3 compares the amino acid sequences of the variable light chain (Vk) and variable heavy chain (VH) of human antibodies, the chimeric and humanized anti-CD19 antibodies. FIG. 3A compares the amino acid sequences of the variable light chain (Vk) of the human antibody, (REIVk; SEQ ID NO:5), a chimeric antibody, (cA19Vk; SEQ ID NO:6), and a humanized antibody, (hA19Vk; SEQ ID NO:7), and FIG. 3B compares the amino acid sequences of the variable heavy chain (VH) of the human antibodies, EU (SEQ ID NO:5) and NEWM (FR4 only; SEQ ID NO:11), the chimeric antibody, (cA19VH; SEQ ID NO:9) and a humanized antibody (hA19VH; SEQ ID NO:10).

FIG. 4 discloses the amino acid sequences of the humanized anti-CD19 antibody, hA19, light chain V gene, (hA19Vk) (FIG. 4A; SEQ ID NO:12 and SEQ ID NO:13), and heavy chain V gene, hA19VH (FIG. 4B; SEQ ID NO:14 and SEQ ID NO:15). The nucleotide sequences are shown in lower case. Numbering of Vk and VH amino acid residues is same as that in FIG. 1.

FIG. 5A shows both unconjugated hA19 (closed triangles) and cA19 (closed circles) blocked the binding of $^{125}$I_hA19 to Raji cells. FIG. 5B shows hA19 (closed circles) and c19 (closed squares) competed equally well for the binding of $^{125}$I_cA19 to Raji cells. Increasing concentrations of either cA19 or hA19 blocked the binding of radiolabled hA19 or cA19 to Raji cells respectively.

DETAILED DESCRIPTION OF THE INVENTION

Figure 2:
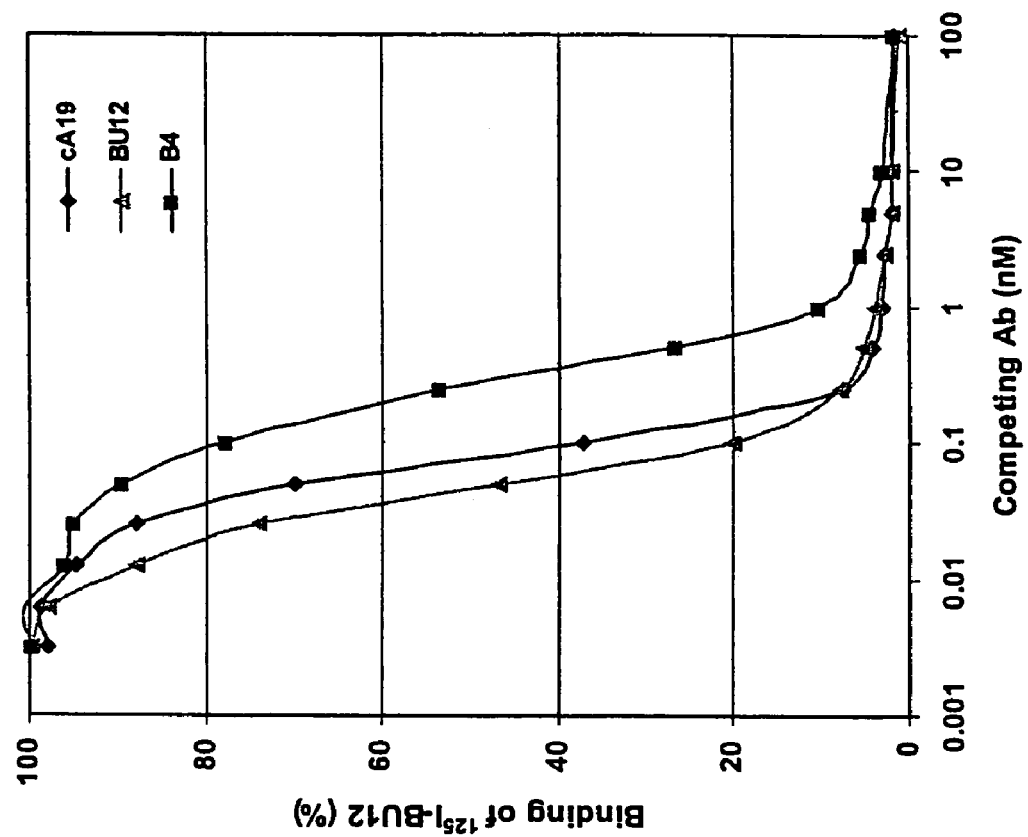
FIG. 2 shows the results of cell surface competitive binding assay to compare the binding specificity of the cA19 antibody with that of other anti-CD19 antibodies, BU12 and B4. Increasing concentrations of cA19 blocked the binding of radiolabled BU12 to Raji cells in a similar fashion as the unlabeled BU12 and B4, indicating these antibodies recognize similar or overlap epitopes of CD19 molecule.
Figure 5:
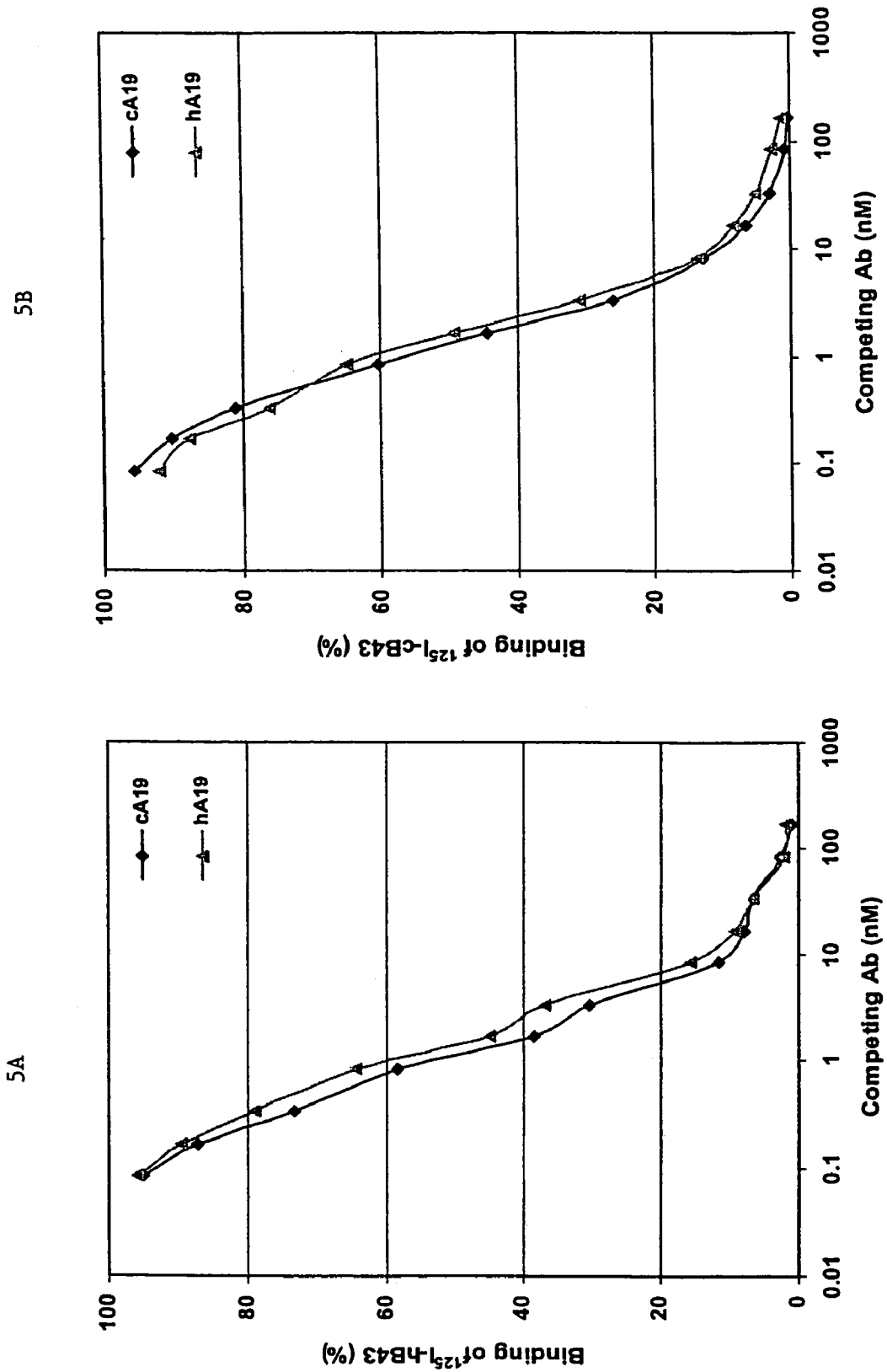
FIG. 5 shows the results of cell surface competitive binding assay to compare the binding specificity and activity of the humanized A19 antibody, hA19, with that of cA19.
Figure 6:
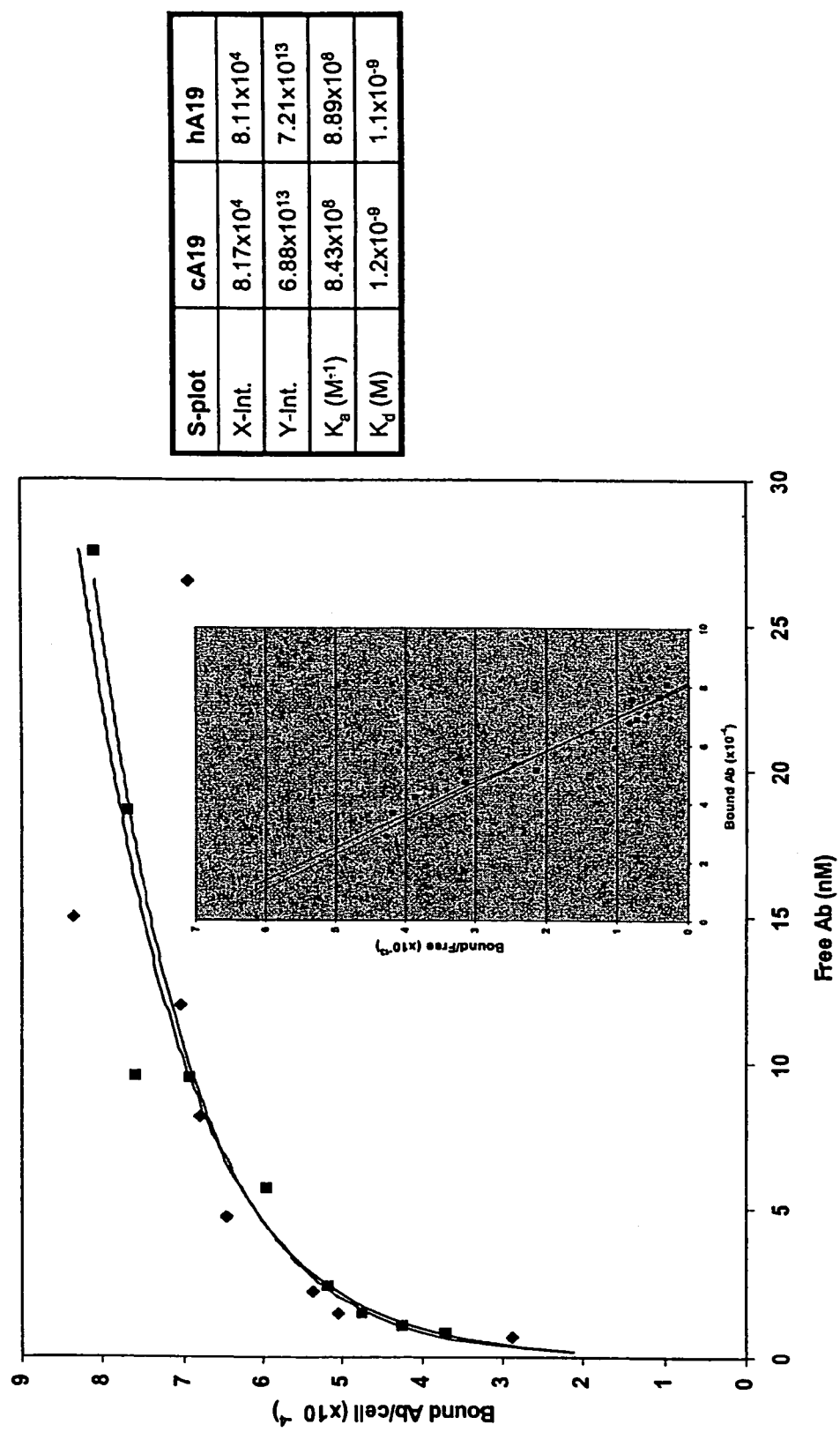
FIG. 6 shows the determination of the Ag-binding affinity (avidity) of the anit-CD19 Ab by the direct cell surface binding and Scatchard plot analysis. Varying concentrations of $^{125}$I-hA19 (diamonds) or $^{112}$I-cA19 (squares) were incubated with Raji cells at $^{40}$ C for 1 h. Total and bound radio activities were counted and analyzed by Scatchard plot as shown in the inset. hA19 showed virtually same binding affinity as cA19. As shown the apparent dissociation constant values were calculated to be 1.1 and 1.2 nM for hA19 and cA19, respectively.

Unless otherwise specified, "a" or "an" as used herein means "one or more."

1. Overview

As discussed above, anti-CD19 antibodies that are unconjugated or labeled with a therapeutic radionuclide, have failed to provide high rates of objective and lasting responses in patients with intermediate or aggressive forms of B-cell lymphoma. The present invention provides a humanized, a chimeric and a human anti-CD19 antibody and antibody fusion proteins thereof useful for treatment of mammalian subjects, humans and domestic animals, alone, as a conjugate or administered in combination with other therapeutic agents, including other naked antibodies and antibody therapeutic conjugates.

The anti-CD19 MAbs of the present invention contain specific murine CDRs or a combination of murine CDRs from more than one murine or chimeric anti-CD19 MAb that have specificity for the CD19 antigen. The anti-CD19 MAbs of the present invention are humanized, chimeric or human MAbs and they contain the amino acids of the CDRs of a murine anti-CD19 MAb and the light and heavy chain constant regions of a human antibody, while retaining substantially the B-cell and B-cell lymphoma and leukemia cell targeting of the murine anti-CD19 MAb. The CDRs of the light chain variable region of the anti-CD19 MAb comprises CDR1 comprising amino acids KASQSVDYDGDSYLN (SEQ ID NO: 16); CDR2 comprising amino acids DASNLVS (SEQ ID NO: 17); and CDR3 comprising amino acids QQSTEDPWT (SEQ IDNO: 18); and the CDRs of the heavy chain variable region of the anti-CD19 MAb comprises CDR1 comprising amino acids SYWMN (SEQ ID NO: 19); CDR2 comprising amino acids QIWPGDGDTNYNGKFKG (SEQ ID NO: 20) and CDR3 comprising amino acids RETTTVGRYYYAMDY (SEQ ID NO: 21).

In a preferred embodiment, the humanized anti-CD19 MAb or fragment thereof of the present invention comprises the CDRs of a murine anti-CD19 MAb and the framework (FR) regions of the light and heavy chain variable regions of a human antibody and the light and heavy chain constant regions of a human antibody, while retaining substantially the B-cell, and B-cell lymphoma and leukemia cell targeting of the parent murine anti-CD19 MAb, and wherein the CDRs of the light chain variable region of the anti-CD 19 MAb comprises CDR1 comprising amino acids KASQSVDYDGDSYLN (SEQ ID NO: 16); CDR2 comprising amino acids DASNLVS (SEQ ID NO: 17); and CDR3 comprising amino acids QQSTEDPWT (SEQ ID NO:18); and the CDRs of the heavy chain variable region of the anti-CD19 MAb comprises CDR1 comprising amino acids SYWMN (SEQ ID NO: 19); CDR2 comprising amino acids QIW- PGDGDTNYNGKFKG (SEQ ID NO: 20) and CDR3 comprising amino acids RETTTVGRYYYAMDY (SEQ ID NO: 21). But the humanized anti-CD19 MAb or fragment thereof may further contain in the FRs of the light and heavy chain variable regions of theantibody at least one amino acid from the corresponding FRs of the murine MAb. Specifically, the humanized anti-CD 19 MAb or fragment thereof contains at least one amino acid residue 5, 27, 28, 40, 48, 91, 94, 107, and 108 of the murine heavy chain variable region of FIG. 4A, designated as hA19VH (SEQ ID NO:10) and of at least one amino acid residue 4, 39, 58, 60, 87, 100, and107 of the murine light chain variable region FIG. 4B, designated hA19Vk (SEQ ID NO:13). Oneor more of the murine amino acid sequences can be maintained in the human FR regions of the light and heavy variable chains if necessary to maintain proper binding or to enhance binding tothe CD 19 antigen. More preferably the humanized anti-CD19 MAb or fragment thereof of the present invention comprises the hA19Vk (SEQ ID NO:13) of FIG. 3A and the hA19VH FIG. 3B(SEQ ID NO:10).

The preferred chimeric anti-CD19 (cA19) MAb or fragment thereof of the present invention comprises the CDRs of a murine anti-CD19 MAb and the FR regions of the light and heavy chain variable regions of the murine anti-CD 19 MAb, i.e., the Fvs of the parental murine MAb, and the light and heavy chain constant regions of a human antibody, wherein the chimeric anti-CD 19 MAb or fragment thereof retains substantially the B-cell, and B-cell lymphoma and leukemia cell targeting of the murine anti-CD 19 MAb, wherein the CDRs of the light chain variable region of the anti-CD19 MAb comprises CDR1 comprising amino acids KASQSVDYDGDSYLN (SEQ ID NO: 16); CDR2 comprising amino acids DASNLVS (SEQ IDNO: 17); and CDR3 comprising amino acids QQSTEDPWT (SEQ ID NO: 18); and the CDRs of the heavy chain variable region of the anti-CD 19 MAb comprises CDR1 comprising amino acids SYWMN (SEQ ID NO: 19); CDR2 comprising amino acids QIWPGDGDTNYNGKFKG (SEQID NO:20) and CDR3 comprising amino acids RETTTVGRYYYAMDY (SEQ ID NO: 21).

More preferably the chimeric anti-CD19 MAb or fragment thereof comprising the complementarity-determining regions (CDRs) of a murine anti-CD19 MAb and the framework(FR) regions of the light and heavy chain variable regions of the murine anti-CD 19 MAb and the light and heavy chain constant regions of a human antibody, wherein the chimeric anti-CD19 MAb or fragment thereof retains substantially the B-cell, and B-cell lymphoma and leukemia cell targeting of the murine anti-CD19 MAb, wherein the CDRs of the light chain variable region of the chimeric anti-CD19 MAb comprises the CDRs shown in FIGS. 2A and 2B, respectively, designated cA19Vk (SEQ ID NO:6) and cA19VH (SEQ ID NO:9).

The present invention also encompasses a human anti-CD19 MAb or fragment thereof comprising the light and heavy chain variable and constant regions of a human antibody, wherein said human anti-CD19 MAb retains substantially the B-cell, and B-cell lymphoma and leukemia cell targeting and cell binding characteristics of a murine anti-CD19 MAb, wherein the CDRs of the light chain variable region of the human anti-CD19 MAb comprises the same CDRs as set forth above for the chimeric and humanized anti-CD19 MAbs and as shown in FIGS. 2A and 2B, and 3A and 3B, respectively.

The present invention is also intended to encompass antibody fusion proteins or fragments thereof comprising at least two anti-CD19 MAbs or fragments thereof, as described above. The antibody fusion protein or fragment thereof of the present invention is also intended to encompass an antibody fusion protein or fragment thereof comprising at least one first anti-CD19 MAb or fragment thereof as described above and at least one second MAb or fragment thereof, other than the anti-CD19 MAb or fragment described above. More preferably this second MAb is a MAb reactive with CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC-1, Ia, HM1.24, HLA-DR, tenascin, an angiogenesis factor, VEGF, PIGF, ED-B fibronectin, an oncogene, an oncogene product, NCA 66a-d, necrosis antigens, Ii, IL-2, T101, TAC, IL-6, TRAIL-R1 (DR4) and TRAIL-R2 (DR5) or a combination thereof, and even an anti-CD19 MAb that is directed to a different epitope than the anti-CD19 MAb described herein. The antibody fusion proteins of the present invention may be composed of one CD19 MAb and one or more of the second MAbs to provide specificity to different antigens, and are described in more detail below.

The humanized, chimeric and human anti-CD19 antibody may possess enhanced affinity binding with the epitope, as well as antitumor and anti-B-cell activity, as a result of CDR mutation and manipulation of the CDR and other sequences in the variable region to obtain a superior therapeutic agent for the treatment of B-cell disorders, including B-cell lymphomas and leukemias and autoimmune diseases. Modification to the binding specificity, affinity or avidity of an antibody is known and described in WO 98/44001, as affinity maturation, and this application summarizes methods of modification and is incorporated in its entirety by reference.

It may also be desirable to modify the antibodies of the present invention to improve effector function, e.g., so as to enhance antigen-dependent cell-mediated cytotoxicity (ADCC) and/or complement dependent cytotoxicity (CDC) of the antagonist. One or more amino acid substitutions or the introduction of cysteine in the Fc region may be made, thereby improving internalization capability and/or increased complement-mediated cell killing and ADCC. See Caron et al., *J. Ex. Med.* 176:1191-1195 (1991) and Shopes, *Brit. J. Immunol.* 148:2918-2022 (1992), incorporated herein by reference in their entirety. An antibody fusion protein may be prepared that has dual Fc regions with both enhanced complement lysis and ADCC capabilities.

The present invention is also directed to DNA sequences comprising a nucleic acid encoding a MAb or fragment thereof selected from the group consisting (a) an anti-CD19 MAb or fragment thereof as described herein, (b) an antibody fusion protein or fragment thereof comprising at least two of the anti-CD19 MAbs or fragments thereof, (c) an antibody fusion protein or fragment thereof comprising at least one first MAb or fragment thereof comprising the anti-CD 19 MAb or fragment thereof as described herein and at least one second MAb or fragment thereof, other than the antiCD19 MAb or fragment thereof, and (d) an antibody fusion protein or fragment thereof comprising at least one first MAb or fragment thereof comprising the anti-CD19 MAb or fragment thereof and at least one second MAb or fragment thereof, wherein the second MAb is a MAb reactive with CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC1, 1a, HM1.24, HLA-DR, tenescin, ED-B fibronectin, IL-6, VEGF, PIGF, TRAIL-R1 (DR4) and TRAIL-R2 (DR5) or a combination thereof.

Also encompassed by the present invention are expression vectors comprising the DNA sequences. These vectors contain the light and heavy chain constant regions and the hinge region of the human immunoglobulin, in the case of vectors far use in preparing the humanized, chimeric and human anti-CD19 MAbs or antibody fusion proteins thereof or fragments thereof. These vectors additionally contain, where required, promoters that express the MAbs in the selected host cell, immunaglobulin enhancers and signal or leader sequences. Vectors that are particularly useful in the present invention are pdHL2 or GS, particularly when used to express a chimeric, humanized or human antibodies, such as IgGs, where the vector codes far the heavy and light chain constant regions and hinge region of IgG1. More preferably, the light and heavy chain constant regions and hinge region are from a human ED myeloma immunoglobulin, where optionally at least one of the amino acid in the allotype positions is changed to that found in a different IgG1 allotype, and wherein optionally amino acid 253 of the heavy chain of EU based on the EU number system may be replaced with alanine. See Edelman et al., *Proc. Natl. Acad. Sci USA* 63: 78-85 (1969), incorporated herein in its entirety by reference.

Host cells containing the DNA sequences encoding the anti-CD 19 MAbs or fragments thereof or antibody fusion proteins or fragments thereof of the present invention or host cells containing the vectors that contain these DNA sequences are encompassed by the present invention. Particularly useful hast cells are mammalian cells, mare specifically lymphocytic cells, such as myeloma cells, discussed in more detail below.

Also encompassed by the present invention is the method of expressing the anti-CD 19 MAb or fragment thereof or antibody fusion protein or fragment thereof comprising: (a) transfecting a mammalian cell with a DNA sequence of encoding the anti-CD19MAbs or fragments thereof or antibody fusion proteins or fragments thereof, and (b) culturing the cell transfected with the DNA sequence that secretes the anti-CD19 or fragment thereof or antibody fusion protein or fragment thereof. Known techniques may be used that include a selection marker on the vector so that host cells that express the MAbs and the marker can be easily selected.

The present invention particularly encompasses B-lymphoma cell and leukemia cell targeting diagnostic or therapeutic conjugates comprising an antibody component comprising an anti-CD19 MAb or fragment thereof or an antibody fusion protein or fragment thereof of the present invention that binds to the B-lymphoma or leukemia cell that is bound to at least one diagnostic or at least one therapeutic agent.

The diagnostic conjugate comprises the antibody component comprising an anti-CD19 MAb or fragment thereof or an antibody fusion protein or fragment thereof, wherein the diagnostic agent comprises at least one photoactive diagnostic agent, and more preferably wherein the label is a radioactive label with an energy between 60 and 4,000 keV or a non-radioactive label. The radioactive label is preferably a gamma-, beta-, and positron-emitting isotope and is selected from the group consisting of $^{125}$I, $^{131}$I, $^{123}$I, $^{124}$I, $^{86}$Y, 186Re, $^{188}$Re, $^{62}$Cu, $^{64}$Cu, $^{111}$In, $^{67}$G, $^{68}$Ga, $^{99m}$Tc, $^{94m}$Tc, $^{18}$F, $^{11}$C, $^{13}$N, $^{15}$0, $^{76}$Br and combinations thereof.

The diagnostic conjugate of the present invention also utilizes a diagnostic agent, such as a contrast agent, for example, such as manganese, iron or gadolinium, and including an ultrasound-enhancing agent. In one embodiment, the ultrasound-enhancing agent is a liposome that comprises a chimerized or humanized anti-CD19 antibody or fragment thereof. Also preferred, the ultrasound enhancing agent is a liposome that is gas filled. Similarly, a bispecific antibody can be conjugated to a contrast agent. For example, the bispecific antibody may comprise more than one image enhancing agent for use in ultrasound imaging. The ultrasound enhancing agent can be a liposome, and preferably, the liposome comprises a bivalent DTPA peptide covalently attached to the outside surface of the liposome. Also preferred, the liposome is gas filled.

The therapeutic conjugate of the present invention comprises an antibody component comprising an antibody fusion protein or fragment thereof, wherein each of said MAbs or fragments thereof are bound to at least one therapeutic agent. The therapeutic conjugate of preferably is selected from the group consisting of a radioactive label, an immunomodulator, a hormone, an enzyme, an oligonucleotide, a photoactive therapeutic agent, a cytotoxic agent, which may be a drug or a toxin, and a combination thereof. The drugs useful in the present invention are those drugs that possess the pharmaceutical property selected from the group consisting of antimitotic, alkylating, antimetabolite, antibiotic, alkaloid, antiangiogenic, apoptotic agents and combinations thereof, as well as antisense oligonucleotides and RNA molecules, such as short double stranded RNA molecules that activate the RNA interference pathway. More specifically, these drugs are selected from the group consisting of nitrogen mustards, ethylenimine derivatives, alkyl sulfonates, nitrosoureas, triazenes, folic acid analogs, COX-2 inhibitors, pyrimidine analogs, purine analogs, antibiotics, enzymes, epipodophyllotoxins, platinum coordination complexes, vinca alkaloids, substituted ureas, methyl hydrazine derivatives, adrenocortical suppressants, thalidomide and its derivatives, antagonists, endostatin, taxols, camptothecins, anthracyclines, taxanes, and their analogs, and a combination thereof. The toxins encompassed by the present invention are selected from the group consisting of ricin, abrin, alpha toxin, saporin, onconase, i.e., ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin.

Other therapeutic agents suitable for use in the present invention include anti-angiogenic agents (or angiogenesis inhibitors). These agents are suitable for use in combination therapy or for conjugating antibodies to, for example, angiostatin, endostatin, vasculostatin, canstatin and maspin, as well as the use of antibodies against angiogenesis factors, such as vascular endothelium growth factor (VEGF), placental growth factor (PlGF), ED-B fibronectin, and against other vascular growth factors. Single and double stranded oligonucleotides are a new class of therapeutic agents, and include, for example, antisense oligonucleotides, such as antisense bcl-2, and molecules, such as double stranded RNA molecules, that activate the RNA interference pathway and cause highly specific inhibition of gene expression, such as inhibition of bcl-2. Inhibition of bcl-2 (and related bcl family molecules) in a cell inhibits the anti-apoptotic activity of bcl-2 and promotes apoptosis of the cell. See Zangemeister-Wittke, *Ann N Y Acad Sci.* 1002:90-4 (2003).

Useful therapeutic conjugates of the present invention are immunomodulators selected from the group consisting of a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins, such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF)), interferon, such as interferons-, alpha-, beta- or gamma-, and stem cell growth factor, such as designated "S1 factor". More specifically, immunomodulator, such as IL-1, IL-2, IL-3, IL-6, IL-10, IL-12, IL-18, IL-21, interferon-, TNF- or a combination thereof are useful in the present invention.

Particularly useful therapeutic conjugates are one or more radioactive labels that have an energy between 60 and 700 keV. Such radioactive labels are selected from the group consisting of $^{225}$Ac, $^{67}$Ga $^{90}$Y, $^{111}$In, $^{131}$I, $^{125}$I, $^{186}$Re, $^{188}$Re, $^{177}$Lu, $^{32}$P, $^{64}$Cu, $^{67}$Cu, $^{212}$Bi, $^{213}$Bi, $^{211}$At and combinations thereof. Other useful therapeutic conjugates are photoactive therapeutic agent, such as a chromogen or dye.

The present invention particularly encompasses methods of treating a B-cell disease in a subject, such as a mammal, including humans, domestic or companion pets, such as dogs and cats. B cell diseases that can be treated by the methods of the invention include any disease which involves unwanted or undesirable B cell growth or activity, and includes malignancies such as lymphoma or leukemia cell disease or an autoimmune disease. The methods involve administering to the subject a therapeutically effective amount of an anti-CD19 MAb or a fragment thereof of the present invention, formulated in a pharmaceutically acceptable vehicle. This therapy utilizes a "naked antibody" that does not have a therapeutic agent bound to it. The administration of the "naked anti-CD19 antibody" can be supplemented by administering to the subject concurrently or sequentially a therapeutically effective amount of another "naked antibody" that binds to or is reactive with another antigen on the surface of the target cell or that has other functions, such as effector functions in the Fc portion of the MAb, that is therapeutic and which is discussed herein. Preferred additional MAbs are at least one humanized, chimeric, human or murine (in the case of non-human animals) MAb selected from the group consisting of a MAb reactive with CD4, CD5, CD8, CD14, CD15, CD19, CD20, CD21, CD22, CD23, CD25, CD30, CD33, CD37, CD38, CD40, CD40L, CD45, CD46, CD52, CD54, CD74, CD80, CD126, CD138, B7, HM1.24, HLA-DR, an angiogenesis factor, tenascin, VEGF, PIGF, ED-B fibronectin, an oncogene, an oncogene product, NCA 66a-d, necrosis antigens, Ii, IL-2, MUC-1, TO1, TAC, IL-6, TRAIL-R1 (DR4) and TRAIL-R2 (DR5) formulated in a pharmaceutically acceptable vehicle.

Both the naked anti-CD19 therapy alone or in combination with other naked MAbs as discussed above can be further supplemented with the administration, either concurrently or sequentially, of a therapeutically effective amount of at least one therapeutic agent, formulated in a pharmaceutically acceptable vehicle. As discussed herein the therapeutic agent may comprise a cytotoxic agent, a radioactive label, an immunomodulator, a hormone, an oligonucleotide (such as an antisense or RNAi oligonucleotide), an enzyme, a photoactive therapeutic agent or a combination thereof, formulated in a pharmaceutically acceptable vehicle.

In another therapeutic method, both the naked anti-CD 19 therapy alone or in combination with other naked MAbs, as discussed above, can be further supplemented with the administration, either concurrently or sequentially, of a therapeutically effective amount of at least one therapeutic conjugate, described herein and formulated in a pharmaceutically acceptable vehicle. The antibody component of the therapeutic conjugate comprises at least one humanized, chimeric, human or murine (for non-human subjects) MAb selected from the group consisting of a MAb reactive with CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, HM1.24, HLA-DR, an angiogenesis factor, tenascin, VEGF, PIGF, ED-B fibronectin, an oncogene, an oncogene product, NCA 66a-d, necrosis antigens, Ii, IL-2, T101, TAC, IL-6, MUC-1, TRAIL-R1 (DR4) and TRAIL-R2 (DR5), formulated in a pharmaceutically acceptable vehicle. As discussed herein the therapeutic agent may comprise a cytotoxic agent, a radioactive label, an immunomodulator, a hormone, a photoactive therapeutic agent or a combination thereof, formulated in a pharmaceutically acceptable vehicle.

As described herein the present invention particurlarly encompasses a method of treating a B-cell lymphoma or leukemia or an autoimmune disease in a subject comprising administering to a subject a therapeutically effective amount of an antibody fusion protein or fragment thereof comprising at least two anti-CD 19 MAbs or fragments thereof of the present invention or comprising at least one anti-CD19 MAb or fragment thereof of the present invention and at least one additional MAb, preferably selected from the group consisting of MAbs reactive with CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, HM1.24, HLA-DR, tenascin, VEGF, PIGF, ED-B fibronectin, MUC-1, an oncogene, an oncogene product, NCA 66a-d, necrosis antigens, Ii, IL-2, T101, TAC, IL-6, TRAIL-R1 (DR4) and TRAIL-R2 (DR5) formulated in a pharmaceutically acceptable vehicle.

This therapeutic method can further be supplemented with the administration to the subject concurrently or sequentially of a therapeutically effective amount of at least one therapeutic agent, formulated in a pharmaceutically acceptable vehicle, wherein the therapeutic agent is preferably a cytotoxic agent, a radioactive label, an immunomodulator, a hormone, a photoactive therapeutic agent or a combination thereof, formulated in a pharmaceutically acceptable vehicle.

Further, the antibody fusion proteins can be administered to a subject concurrently or sequentially a therapeutically effective amount of a therapeutic conjugate comprising at least one MAb bound to at least one therapeutic agent, wherein said MAb component of the conjugate preferably comprises at least one humanized, chimeric, human or murine (for non-human subjects) MAb selected from the group consisting of a MAb reactive with CD4, CD5, CD8, CD 14, CD15, CD19, CD20, CD21, CD22, CD23, CD25, CD33, CD37, CD38, CD40, CD40L, CD46, CD52, CD54, CD74, CD80, CD126, CD138, B7, MUC1, Ia, HM1.24, HLA-DR, tenascin, VEGF, PIGF, ED-B fibronectin, an oncogene, an oncogene product, NCA 66a-d, necrosis antigens, Ii, IL-2, IL-6, T101, TAC, IL-6, TRAIL-R1 (DR4) and TRAIL-R2 (DR5) formulated in a pharmaceutically acceptable vehicle. The antibody fusion protein itself can be conjugated to a therapeutic agent and thus provides a vehicle to attach more than one therapeutic agent to an antibody component and these therapeutic agents can be a combination of different recited agents or combinations of the same agents, such as two different therapeutic radioactive labels.

Also encompassed by the present invention is a method of diagnosing a B-cell lymphoma or leukemia in a subject comprising administering to the subject, such as a mammal, including humans and domestic and companion pets, such as dogs, cats, rabbits, guinea pigs, a diagnostic conjugate comprising an anti-CD19 MAb or fragment thereof or an antibody fusion protein or fragment thereof of the present invention that binds to the lymphoma or leukemia cell, wherein the anti-CD 19 MAb or fragment thereof or antibody fusion protein or fragment thereof is bound to at least one diagnostic agent, formulated in a pharmaceutically acceptable vehicle. The useful diagnostic agents are described herein.

2. Definitions

In the description that follows, a number of terms are used and the following definitions are provided to facilitate understanding of the present invention.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab)$_2$, F(ab)$_2$, Fab, Fab, Fv, sFv and the like. Regardless of structure, an antibody fragment binds with the same antigen that is recognized by the intact antibody. For example, an anti-CD19 monoclonal antibody fragment binds with an epitope of CD19. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A naked antibody is generally an entire antibody which is not conjugated to a therapeutic agent. This is so because the Fc portion of the antibody molecule provides effector functions, such as complement fixation and ADCC (antibody dependent cell cytotoxicity), which set mechanisms into action that may result in cell lysis. However, it is possible that the Fc portion is not required for therapeutic function, with other mechanisms, such as apoptosis, coming into play. Naked antibodies include both polyclonal and monoclonal antibodies, as well as certain recombinant antibodies, such as chimeric, humanized or human antibodies.

A chimeric antibody is a recombinant protein that contains the variable domains including the complementarity determining regions (CDRs) of an antibody derived from one species, preferably a rodent antibody, while the constant domains of the antibody molecule is derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, is transferred from the heavy and light variable chains of the rodent antibody into human heavy and light variable domains. The constant domains of the antibody molecule is derived from those of a human antibody.

A human antibody is an antibody obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993).

Human antibodies may also be generated by in vitro activated B cells. See U.S. Pat. Nos. 5,567,610 and 5,229,275, which are incoporated in their entirety by reference.

A therapeutic agent is a molecule or atom which is administered separately, concurrently or sequentially with an antibody moiety or conjugated to an antibody moiety, i.e., antibody or antibody fragment, or a sub fragment, and is useful in the treatment of a disease. Examples of therapeutic agents include antibodies, antibody fragments, drugs, toxins, enzymes, oligonucleotides, antisense and RNAi oligonucleotides, nucleases, hormones, immunomodulators, chelators, boron compounds, photoactive agents or dyes and radioisotopes.

A diagnostic agent is a molecule or atom which is administered conjugated to an antibody moiety, i.e., antibody or antibody fragment, or subfragment, and is useful in diagnosing a disease by locating the cells containing the antigen. Useful diagnostic agents include, but are not limited to, radioisotopes, dyes (such as with the biotin-streptavidin complex), contrast agents, ultrasound-enhancing agents, optical-enhancing agents, fluorescent compounds or molecules and enhancing agents (e.g. paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic agents are selected from the group consisting of radioisotopes, enhancing agents for use in magnetic resonance imaging, ultrasound, and fluorescent compunds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates are coupled to the peptide antigens using standard chemistries. The chelate is normally linked to the antibody by a group which enables formation of a bond to the molecule with minimal loss of immunoreactivity and minimal aggregation and/or internal cross-linking. Other, more unusual, methods and reagents for conjugating chelates to antibodies are disclosed in U.S. Pat. No. 4,824,659 to Hawthorne, entitled "Antibody Conjugates", issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}I$, $^{131}I$, $^{123}I$, $^{124}I$, $^{62}Cu$ $^{62}$Cu, $^{18}$F, $^{111}$In, $^{67}$Ga, $^{68}$Ga, $^{99m}$Tc, $^{94m}$Tc, $^{11}$C, $^{13}$N, $^{15}$O, $^{76}$Br, for radio-imaging. The same chelates, when complexed with non-radioactive metals, such as manganese, iron and gadolinium are useful for MRI, when used along with the antibodies of the invention. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macro cyclic polyethers, which are of interest for stably binding nuclides, such as $^{223}$Ra for RAIT are encompassed by the invention.

An immunoconjugate is a conjugate of an antibody component with a therapeutic or diagnostic agent. The diagnostic agent can comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope.

An expression vector is a DNA molecules comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells, as well as an transgenic animal, that have been genetically engineered to contain the cloned gene(s) in the chromosome or genome of the host cell or cells of the host cells. Suitable mammalian host cells include myeloma cells, such as SP2/0 cells, and NS0 cells, as well as Chinese Hamster Ovary (CH0) cells, hybridoma cell lines and other mammalian host cell useful for expressing antibodies. Also particularly useful to express MAbs and other fusion proteins, is a human cell line, PER.C6 disclosed in WO 0063403 A2, which produces 2 to 200-fold more recombinant protein as compared to conventional mammalian cell lines, such as CHO, COS, Vero, Hela, BHK and SP2-cell lines. Special transgenic animals with a modified immune system are particularly useful for making fully human antibodies.

As used herein, the term antibody fusion protein is a recombinantly produced antigen-binding molecule in which two or more of the same or different single-chain antibody or antibody fragment segments with the same or different specificities are linked. Valency of the fusion protein indicates how many binding arms or sites the fusion protein has to a single antigen or epitope; i.e., monovalent, bivalent, trivalent or mutlivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., mono-specific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds with one epitope, for example a diabody with two binding site reactive with the same antigen. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

A multispecific antibody is an antibody that can bind simultaneously to at least two targets that are of different structure, e.g., two different antigens, two different epitopes on the same antigen, or a hapten and/or an antigen or epitope. One specificity would be for a B-cell, T-cell, myeloid-, plasma-, and mast-cell antigen or epitope. Another specificity could be to a different antigen on the same cell type, such as CD20, CDI9, CD20, CD21, CD23, CD46, CD80, HLA-DR, CD74, and CD22 on B-cells. Multispecific, multivalent antibodies are constructs that have more than one binding site, and the binding sites are of different specificity. For example, a diabody, where one binding site reacts with one antigen and the other with another antigen.

A bispecific antibody is an antibody that can bind simultaneously to two targets which are of different structure. Bispecific antibodies (bsAb) and bispecific antibody fragments (bsFab) have at least one arm that specifically binds to, for example, a B-cell, T-cell, myeloid-, plasma-, and mast-cell antigen or epitope and at least one other arm that specifically binds to a targetable conjugate that bears a therapeutic or diagnostic agent. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with a binding site for one antigen and two scFv with two binding sites for a second antigen.

Caninized or felinized antibodies are recombinant proteins in which rodent (or another species) complementarity determining regions of a monoclonal antibody have been transferred from heavy and light variable chains of rodent (or another species) immunoglobulin into a dog or cat, respectively, immunoglobulin variable domain.

Domestic animals include large animals such as horses, cattle, sheep, goats, llamas, alpacas, and pigs, as well as companion animals. In a preferred embodiment, the domestic animal is a horse.

Companion animals include animals kept as pets. These are primarily dogs and cats, although small rodents, such as guinea pigs, hamsters, rats, and ferrets, are also included, as are subhuman primates such as monkeys. In a preferred embodiment the companion animal is a dog or a cat.

3. Preparation of Monoclonal Antibodies Including Chimeric, Humanized and Human Antibodies Monoclonal antibodies (MAbs) are a homogeneous population of antibodies to a particular antigen and the antibody comprises only one type of antigen binding site and binds to only one epitope on an antigenic determinant. Rodent monoclonal antibodies to specific antigens may be obtained by methods known to those skilled in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are wen known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions.

General techniques for cloning murine immunoglobulin variable domains are described, for example, by the publication of Orlandi et al., *Proc. Natfl Acad. Sci. USA* 86: 3833 (1989), which is incorporated by reference in its entirety. Techniques for constructing chimeric antibodies are well known to those of skill in the art. As an example, Leung et at., *Hybridoma* 13:469 (1994), describe how they produced an LL2 chimera by combining DNA sequences encoding the V and $V_H$ domains of LL2 monoclonal antibody, an anti-CD22 antibody, with respective human and $IgG_1$ constant region domains. This publication also provides the nucleotide sequences of the LL2 light and heavy chain variable regions, V and $V_H$, respectively. Techniques for producing humanized MAbs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

A chimeric antibody is a recombinant protein that contains the variable domains including the CDRs derived from one species of animal, such as a rodent antibody, while the remainder of the antibody molecule; i.e., the constant domains, is derived from a human antibody. Accordingly, a chimeric monoclonal antibody can also be humanized by replacing the sequences of the murine FR in the variable domains of the chimeric MAb with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an anatibody that possesses good binding affinity to its epitope. See, for example, Tempest et al., *Biotechnology* 9:266 (1991) and Verhoeyen et al., *Science* 239: 1534 (1988). Further, the affinity of humanized, chimeric and human MAbs to a specific epitope can be increased by mutagenesis of the CDRs, so that a lower dose of antibody may be as effective as a higher dose of a lower affinity MAb prior to mutagenesis. See for example, WO0029584A1.

Another method for producing the antibodies of the present invention is by production in the milk of transgenic livestock. See, e.g., Colman, A., *Biochem. Soc. Symp.*, 63: 141-147, 1998; U.S. Pat. No. 5,827,690, both of which are incorporated in their entirety by reference. Two DNA constructs are prepared which contain, respectively, DNA segments encoding paired immunoglobulin heavy and light chains. The DNA segments are cloned into expression vectors which contain a promoter sequence that is preferentially expressed in mammary epithelial cells. Examples include, but are not limited to, promoters from rabbit, cow and sheep casein genes, the cow-lactoglobulin gene, the sheep-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A fully human antibody of the present invention, i.e., human anti-CD19 MAbs or other human antibodies, such as anti-CD22, anti-CD19, anti-CD23, anti-CD20 or anti-CD21 MAbs for combination therapy with humanized, chimeric or human anti-CD19 antibodies, can be obtained from a transgenic non-human animal. See, e.g., Mendez et al., *Nature Genetics,* 15: 146-156 (1997); U.S. Pat. No. 5,633,425, which are incorporated in their entirety by reference. For example, a human antibody can be recovered from a transgenic mouse possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the Y AC through their germline and are bred with mice deficient in murine antibody production. Breeding the two transgenic strains, one containing the human heavy-chain loci and the other containing the human light-chain loci, creates progeny which produce human antibodies in response to immunization.

Further recent methods for producing bispecific MAbs include engineered recombinant MAbs which have additional cysteine residues so that they crosslink more strongly than the more common immunoglobulin isotypes. See, e.g., FitzGerald et al., Protein Eng. 10(10):1221-1225, 1997. Another approach is to engineer recombinant fusion proteins linking two or more different single-chain antibody or antibody fragment segments with the needed dual specificities. See, e.g., Coloma et al., Nature Biotech. 15:159-163, 1997. A variety of bispecific fusion proteins can be produced using molecular engineering. See, for example, Alt et al., FEBS Lett. 454:90-4 (1999), which is incorporated herein by reference in its entirety. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

Bispecific fusion proteins linking two or more different single-chain antibodies or antibody fragments are produced in similar manner. Recombinant methods can be used to produce a variety of fusion proteins. For example a fusion protein comprising a Fab fragment derived from a humanized monoclonal anti-CD19 antibody and a scFv derived from a murine anti-diDTPA can be produced. A flexible linker, such as GGGS connects the scFv to the constant region of the heavy chain of the anti-CD19 antibody. Alternatively, the scFv can be connected to the constant region of the light chain of another humanized antibody. Appropriate linker sequences necessary for the in-frame connection of the heavy chain Fd to the scFv are introduced into the VL and VK domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the VH region of an anti-CD19 antibody. The resulting vector can be used to transfect an appropriate host cell, such as a mammalian cell for the expression of the bispecific fusion protein.

4. Production of Antibody Fragments

Antibody fragments which recognize specific epitopes can be generated by known techniques. The antibody fragments are antigen binding portions of an antibody, such as $F(ab')_2$, Fab', Fab, Fv, sFv and the like. Other antibody fragments include, but are not limited to: the $F(ab)'_2$ fragments which can be produced by pepsin digestion of the antibody molecule and the Fab' fragments, which can be generated by reducing disulfide bridges of the F(ab)'2 fragments. Alternatively, Fab' expression expression libraries can be constructed (Huse et al., 1989, *Science,* 246:1274-1281) to allow rapid and easy identification of monoclonal Fab' fragments with the desired specificity. The present invention encompasses antibodies and antibody fragments.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. No. 4,704,692, U.S. Pat. No. 4,946,778, R. Raag and M. Whitlow, "*Single Chain Fvs.*" FASEB Vol 9:73-80 (1995) and R. E. Bird and B. W. Walker, "*Single Chain Antibody Variable Regions,*" TIBTECH, Vol 9: 132-137 (1991). These references are incorporated herein by reference.

An antibody fragment can be prepared by proteolytic hydrolysis of the full-length antibody or by expression in *E. coli* or another host of the DNA coding for the fragment. An antibody fragment can be obtained by pepsin or papain digestion of full length antibodies by conventional methods. For example, an antibody fragment can be produced by enzymatic cleavage of antibodies with pepsin to provide a 5S fragment denoted $F(ab)_2$. This fragment can be further cleaved using a thiol reducing agent, and optionally a blocking group for the sulfhydryl groups resulting from cleavage of disulfide linkages, to produce 3.5S Fab monovalent fragments. Alternatively, an enzymatic cleavage using papain produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Another form of an antibody fragment is a peptide coding for a single complementarity-determining region (CDR). A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991); Courtenay-Luck, "Genetic Manipulation of Monoctonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

5. Multispecific and Multivalent Antibodies

The anti-CD19 antibodies, as well as other antibodies with different specificities for use in combination therapy, described herein, can also be made as multispecific antibodies (comprising at least one binding site to a CD19 epitope or antigen and at least one binding site to another epitope on CD19 or another antigen) and multivalent antibodies (comprising mutliple binding sites to the same epitope or antigen).

The present invention provides a bispecific antibody or antibody fragment having at least a binding region that specifically binds a targeted cell marker and at least one other binding region that specifically binds a targetable conjugate. The targetable conjugate comprises a carrier portion which comprises or bears at least one epitope recognized by at least one binding region of the bispecific antibody or antibody fragment.

A variety of recombinant methods can be used to produce bispecific antibodies and antibody fragments as described above.

An anti-CD 19 multivalent antibody is also contemplated in the present invention. This multivalent target binding protein is constructed by association of a first and a second polypeptide. The first polypeptide comprises a first single chain Fv molecule covalently linked to a first immunoglobulin-like domain which preferably is an immunoglobulin light chain variable region domain. The second polypeptide comprises a second single chain Fv molecule covalently linked to a second immunoglobulin-like domain which preferably is an immunoglobulin heavy chain variable region domain. Each of the first and second single chain Fv molecules forms a target binding site, and the first and second immunoglobulin-like domains associate to form a third target binding site.

A single chain Fv molecule with the VL-L-VH configuration, wherein L is a linker, may associate with another single chain Fv molecule with the VH-L-VL configuration to form a bivalent dimer. In this case, the VL domain of the first scFv and the VH domain of the second scFv molecule associate to form one target binding site, while the VH domain of the first scFv and the VL domain of the second scFv associate to form the other target binding site.

Another embodiment of the present invention is a CD19 bispecific, trivalent targeting protein comprising two heterologous polypeptide chains associated noncovalently to form three binding sites, two of which have affinity for one target and a third which has affinity for a hapten that can be made and attached to a carrier for a diagnostic and/or therapeutic agent. Preferably, the binding protein has two CD19 binding sites and one CD22 binding site. The bispecific, trivalent targeting agents have two different scFvs, one scFv contains two $V_H$ domains from one antibody connected by a short linker to the $V_L$ domain of another antibody and the second scFv contains two $V_L$ domains from the first antibody connected by a short linker to the $V_H$ domain of the other antibody. The methods for generating multivalent, multispecific agents from $V_H$ and $V_L$ domains provide that individual chains synthesized from a DNA plasmid in a host organism are composed entirely of $V_H$ domains (the $V_H$-chain) or entirely of $V_L$ domains (the $V_L$-chain) in such a way that any agent of multivalency and multispecificity can be produced by non-covalent association of one $V_H$-chain with one $V_L$-chain. For example, forming a trivalent, trispecific agent, the $V_H$-chain will consist of the amino acid sequences of three $V_H$ domains, each from an antibody of different specificity, joined by peptide linkers of variable lengths, and the $V_L$-chain will consist of complementary $V_L$ domains, joined by peptide linkers similar to those used for the $V_H$-chain. Since the $V_H$ and $V_L$ domains of antibodies associate in an anti-parallel fashion, the preferred method in this invention has the $V_L$ domains in the $V_L$-chain arranged in the reverse order of the $V_H$ domains in the $V_H$-chain.

6. Diabodies, Triabodies and Tetrabodies

The anti-CD19 antibodies of the present invention can also be used to prepare functional bispecific single-chain antibodies (bscAb), also called diabodies, and can be produced in mammalian cells using recombinant methods. See, e.g., Mack et al., *Proc. Natl. Acad. Sci.*, 92: 7021-7025, 1995, incorporated. For example, bscAb are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the $(Gly_4\text{-}Ser_1)_3$ linker, and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into chinese hamster ovary cells. Bispecific fusion proteins are prepared in a similar manner. Bispecific single-chain antibodies and bispecific fusion proteins are included within the scope of the present invention.

For example, a humanized, chimeric or human anti-CD19 monoclonal antibody can be used to produce antigen specific diabodies, triabodies, and tetrabodies. The monospecific diabodies, triabodies, and tetrabodies bind selectively to targeted antigens and as the number of binding sites on the molecule increases, the affinity for the target cell increases and a longer residence time is observed at the desired location. For diabodies, the two chains comprising the $V_H$ polypeptide of the humanized CD19 MAb connected to the $V_K$ polypeptide of the humanized CD19 MAb by a five amino acid residue linker are utilized. Each chain forms one half of the humanized CD19 diabody. In the case of tria bodies, the three chains comprising $V_H$ polypeptide of the humanized CD19 MAb connected to the $V_K$ polypeptide of the humanized CD19 MAb by no linker are utilized. Each chain forms one third of the hCD19 triabody.

The ultimate use of the bispecific diabodies described herein is for pretargeting CD 19 positive tumors for subsequent specific delivery of diagnostic or therapeutic agents. These diabodies bind selectively to targeted antigens allowing for increased affinity and a longer residence time at the desired location. Moreover, non-antigen bound diabodies are cleared from the body quickly and exposure of normal tissues is minimized. Bispecific antibody point mutations for enhancing the rate of clearance can be found in U.S. Provisional Application No. 60/361,037 to Qu et al., which is incorporated herein by reference in its entirety. Bispecific diabodies for affinity enhancement are disclosed in U.S. application Ser. No. 10/270,071 (Rossi et al.), Ser. No. 10/270,073 (Rossi et al.) and Ser. No. 10/328,190 (Rossi et al.), which are incorporated herein by reference in their entirety. The diagnostic and therapeutic agents can include isotopes, drugs, toxins, cytokines, hormones, enzymes, oligonucleotides, growth factors, conjugates, radionuclides, and metals. For example, gadolinium metal is used for magnetic resonance imaging (MRI). Examples of radio nuclides are $^{225}Ac$, $^{18}F$, $^{68}Ga$, $^{67}Ga$, $^{90}Y$, $^{86}Y$, $^{111}In$, $^{131}I$, $^{125}I$, $^{123}I$, $^{99m}Tc$, $^{99m}Tc$, $^{186}Re$, $^{188}Re$, $^{177}Lu$, $^{62}Cu$, $^{64}Cu$, $^{67}Cu$, $^{212}Bi$, $^{213}Bi$, $^{32}P$, $^{11}C$, $^{13}N$, $^{15}O$, $^{76}Br$, and $^{211}At$. Other radionuclides are also available as diagnostic and therapeutic agents, especially those in the energy range of 60 to 4,000 keV.

More recently, a tetravalent tandem diabody (termed tandab) with dual specificity has also been reported (Cochlovius et al., Cancer Research (2000) 60: 4336-4341). The bispecific tandab is a dimer of two identical polypeptides, each containing four variable domains of two different antibodies ($V_{H1}$, $V_{L1}$, $V_{H2}$, $V_{L2}$) linked in an orientation to facilitate the formation of two potential binding sites for each of the two different specificities upon self-association.

7. Conjugated Multivalent and Multispecific Anti-CD19 Antibodies

In another embodiment of the instant invention is a conjugated multivalent anti-CD19 antibody. Compositions and methods for multivalent, multispecific agents are described in Rossi et al., U.S. Patent Application Ser. No.: 60/436,359, filed Dec. 24, 2002, and U.S. Patent Application Ser. No. 60/464,532, filed Apr. 23, 2003, which are incorporated herein by reference in its entirety.

Additional amino acid residues may be added to either the N- or C-terminus of the first or the second polypeptide. The additional amino acid residues may comprise a peptide tag, a signal peptide, a cytokine, an enzyme (for example, a prodrug activating enzyme), a hormone, a peptide toxin, such as pseudomonas extoxin, a peptide drug, a cytotoxic protein or other functional proteins. As used herein, a functional protein is a protein which has a biological function.

In one embodiment, drugs, toxins, radioactive compounds, enzymes, hormones, oligonucleotides, cytotoxic proteins, chelates, cytokines and other functional agents may be conjugated to the multivalent target binding protein, preferably through covalent attachments to the side chains of the amino acid residues of the multivalent target binding protein, for example amine, carboxyl, phenyl, thiol or hydroxyl groups. Various conventional linkers may be used for this purpose, for example, diisocyanates, diisothiocyanates, bis(hydroxysuccinimide) esters, carbodiimides, maleimide-hydroxysuccinimide esters, glutaraldehyde and the like. Conjugation of agents to the multivalent protein preferably does not significantly affect the protein's binding specificity or affinity to its target. As used herein, a functional agent is an agent which has a biological function. A preferred functional agent is a cytotoxic agent.

As discussed above, enzymes are also useful therapeutic agents. For example, alkaline phosphatase for use in combination with phosphate-containing prodrugs (U.S. Pat. No. 4,975,278); arylsulfatase for use in combination with sulfate-containing prodrugs (U.S. Pat. No. 5,270,196); peptidases and proteases, such as *serratia* protease, thermolysin, subtilisin, carboxypeptidase (U.S. Pat. Nos. 5,660,829; 5,587,161; 5,405,990) and cathepsins (including cathepsin B and L), for use in combination with peptide-based prodrugs; D-alanyl-carboxypeptidases for use in combination with D-amino acid-modified prodrugs; carbohydrate-cleaving enzymes such as beta-galactosidase and neuraminidase for use in combination with glycosylated prodrugs (U.S. Pat. Nos. 5,561, 119; 5,646,298); beta.-Iactamase for use in combination with beta-Iactam-containing prodrugs; penicillin amidases, such as penicillin-V-amidase (U.S. Pat. No. 4,975,278) or penicillin-G-amidase, for use in combination with drugs derivatized at their amino nitrogens with phenoxyacetamide or phenylacetamide groups; and cytosine deaminase (U.S. Pat. Nos. 5,338,678; 5,545,548) for use in combination with 5-fluorocytosine-based prodrugs (U.S. Pat. No. 4,975,278), are suitable therapeutic agents for the present invention.

In still other embodiments, bispecific antibody-directed delivery of therapeutics or prodrug polymers to in vivo targets can be combined with bispecific antibody delivery of radionuclides, such that combination chemotherapy and radioimmunotherapy is achieved. Each therapy can be conjugated to the targetable conjugate and administered simultaneously, or the nuclide can be given as part of a first targetable conjugate and the drug given in a later step as part of a second targetable conjugate.

In another embodiment, cytotoxic agents may be conjugated to a polymeric carrier, and the polymeric carrier may subsequently be conjugated to the multivalent target binding protein. For this method, see Ryser et al., *Proc. Natl. Acad. Sci. USA*, 75:3867-3870,1978, U.S. Pat. No. 4,699,784 and U.S. Pat. No. 4,046,722, which are incorporated herein by reference. Conjugation preferably does not significantly affect the binding specificity or affinity of the multivalent binding protein.

8. Humanized, Chimeric and Human Antibodies Use for Treatment and Diagnosis

Humanized, chimeric and human monoclonal antibodies, i.e., anti-CD19 MAbs and other MAbs described herein, in accordance with this invention, are suitable for use in therapeutic methods and diagnostic methods. Accordingly, the present invention contemplates the administration of the humanized, chimeric and human antibodies of the present invention alone as a naked antibody or administered as a multimodal therapy, temporally according to a dosing regimen, but not conjugated to, a therapeutic agent. The efficacy of the naked anti-CD19 MAbs can be enhanced by supplementing naked antibodies with one or more other naked antibodies, i.e., MAbs to specific antigens, such as CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC1, Ia, HM1.24, HLA-DR, tenascin, VEGF, PIGF, ED-B fibronectin, an oncogene, an oncogene product, NCA 66a-d, necrosis antigens, Ii, IL-2, T101, TAC, IL-6, TRAIL-R1 (DR4) and TRAIL-R2 (DR5) with one or more immunoconjugates of anti-CD19, or antibodies to theses recited antigens, conjugated with therapeutic agents, including drugs, toxins, immunomodulators, hormones, enzymes, oligonucleotides, therapeutic radionuclides, etc., with one or more therapeutic agents, including drugs, toxins, enzymes, oligonucleotides, immunomodulators, hormones, therapeutic radionuclides, etc., administered concurrently or sequentially or according to a prescribed dosing regimen, with the MAbs. Preferred B-cell antigens include those equivalent to human CDl9, CD20, CD21, CD22, CD23, CD46, CD52, CD74, CD80, and CD5 antigens. Preferred T-cell antigens include those equivalent to human CD4, CD8 and CD25 (the IL-2 receptor) antigens. An equivalent to HLA-DR antigen can be used in treatment of both B-cell and T-cell disorders. Particularly preferred B-cell antigens are those equivalent to human CD19, CD20, CD22, CD21, CD23, CD74, CD80, and HLA-DR antigens. Particularly preferred T-cell antigens are those equivalent to human CD4, CD8 and CD25 antigens. CD46 is an antigen on the surface of cancer cells that block complement-dependent lysis (CDC).

Further, the present invention contemplates the administration of an immunoconjugate for diagnostic and therapeutic uses in B cell lymphomas and other disease or disorders. An immunoconjugate, as described herein, is a molecule comprising an antibody component and a therapeutic or diagnostic agent, including a peptide which may bear the diagnostic or therapeutic agent. An immunoconjugate retains the immunoreactivity of the antibody component, i.e., the antibody moiety has about the same or slightly reduced ability to bind the cognate antigen after conjugation as before conjugation.

A wide variety of diagnostic and therapeutic reagents can be advantageously conjugated to the antibodies of the invention. The therapeutic agents recited here are those agents that also are useful for administration separately with the naked antibody as described above. Therapeutic agents include, for example, chemotherapeutic drugs such as vinca alkaloids, anthracyclines, epidophyllotoxins, taxanes, antimetabolites, alkylating agents, antibiotics, COX-2 inhibitors, antimitotics, antiangiogenic and apoptotoic agents, particularly doxorubicin, methotrexate, taxol, CPT-11, camptothecans, proteosome inhibitors, and others from these and other classes of anticancer agents, thalidomide and derivates, oligonucleotides, particularly antisense and RNAi oligonucleotides (e.g., against bcl-2), and the like. Other useful cancer chemotherapeutic drugs for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, enzymes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Additionally, a chelator such as DTPA, DOTA, TETA, or NOTA or a suitable peptide, to which a detectable label, such as a fluorescent molecule, or cytotoxic agent, such as a heavy metal or radionuclide, can be conjugated. For example, a therapeutically useful immunoconjugate can be obtained by conjugating a photoactive agent or dye to an antibody composite. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, Chem. Britain 22:430 (1986)). Moreover, monoclonal antibodies have been coupled with photoactivated dyes for achieving phototherapy. Mew et al., J. Immunoi. 130:1473 (1983); idem., Cancer Res. 45:4380 (1985); Oseroff et al., Proc. Natl. Acad. Sci. USA 83:8744 (1986); idem., Photochem. Photohiol. 46:83 (1987); Hasan et al., Prog. Clin. Biol. Res. 288:471 (1989); Tatsuta et al., Lasers Surg Med. 9:422 (1989); Pelegrin et al., Cancer 67:2529 (1991). However, these earlier studies did not include use of endoscopic therapy applications, especially with the use of antibody fragments or subfragments. Thus, the present invention contemplates the therapeutic use of immunoconjugates comprising photo active agents or dyes.

Also contemplated by the present invention are the use of radioactive and non-radioactive agents as diagnostic agents. A suitable non-radioactive diagnostic agent is a contrast agent suitable for magnetic resonance imaging, computed tomography or ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies of the invention. See U.S. Ser. No. 09/921,290 filed on Oct. 10, 2001, which is incorporated in its entirety by reference.

Furthermore, a radiolabeled antibody or immunoconjugate may comprise a gamma-emitting radioisotope or a positron-emitter useful for diagnostic imaging. Suitable radioisotopes, particularly in the energy range of 60 to 4,000 keV, include $^{131}$I, $^{123}$I, $^{124}$I, $^{86}$Y, $^{62}$Cu, $^{64}$Cu, $^{111}$In, $^{67}$Ga, $^{68}$Ga, $^{99m}$Tc, $^{94m}$Tc, $^{18}$F, $^{11}$C, $^{13}$N, $^{15}$O, $^{75}$Br, and the like. See for example, U.S. patent application entitled "Labeling Targeting Agents with Gallium-68"—Inventors G. L. Griffiths and W. J. McBride, (U.S. Provisional Application No. 60/342,104), which discloses positron emitters, such as $^{18}$F, $^{68}$Ga, $^{94m}$Tc. and the like, for imaging purposes and which is incorporated in its entirety by reference.

A toxin, such as Pseudomonas exotoxin, may also be complexed to or form the therapeutic agent portion of an antibody fusion protein of an anti-CD19 antibody of the present invention. Other toxins suitably employed in the preparation of such conjugates or other fusion proteins, include ricin, abrin, ribonuclease (RNase), DNase I, Staphylococcal enterotoxin-A, pokeweed antiviral protein, gelonin, diphtherin toxin, Pseudomonas exotoxin, and Pseudomonas endotoxin. See, for example, Pastan et al., Cell 47:641 (1986), and Goldenberg, C A—A Cancer Journal for Clinicians 44:43 (1994). Additional toxins suitable for use in the present invention are known to those of skill in the art and are disclosed in U.S. Pat. No. 6,077,499, which is incorporated in its entirety by reference.

An immunomodulator, such as a cytokine may also be conjugated to, or form the therapeutic agent portion of an antibody fusion protein or be administered with the humanized anti-CD19 antibodies of the present invention. Suitable cytokines for the present invention include, but are not limited to, interferons and interleukins, as described below.

9. Preparation of Immunoconjugates

Any of the antibodies or antibody fusion proteins of the present invention can be conjugated with one or more therapeutic or diagnostic agents. Generally, one therapeutic or diagnostic agent is attached to each antibody or antibody fragment but more than one therapeutic agent or diagnostic agent can be attached to the same antibody or antibody fragment. The antibody fusion proteins of the present invention comprise two or more antibodies or fragments thereof and each of the antibodies that compose this fusion protein can contain a therapeutic agent or diagnostic agent. Additionally, one or more of the antibodies of the antibody fusion protein can have more than one therapeutic of diagnostic agent attached. Further, the therapeutic agents do not need to be the same but can be different therapeutic agents. For example, one can attach a drug and a radioisotope to the same fusion protein. Particularly, an IgG can be radiolabeled with $^{131}$I and attached to a drug. The $^{131}$I can be incorporated into the tyrosine of the IgG and the drug attached to the epsilon amino group of the IgG lysines. Both therapeutic and diagnostic agents also can be attached to reduced SH groups and to the carbohydrate side chains.

Bispecific antibodies of the present invention are useful in pretargeting methods and provide a preferred way to deliver two therapeutic agents or two diagnostic agents to a subject. U.S. Ser. No. 09/382,186 discloses a method of pretargeting using a bispecific antibody, in which the bispecific antibody is labeled with $^{125}$I and delivered to a subject, followed by a divalent peptide labeled with $^{99m}$Tc. U.S. Ser. Nos. 09/382,186 and 09/337,756 discloses a method of pre targeting using a bispecific antibody, in which the bispecific antibody is labeled with $^{125}$I and delivered to a subject, followed by a divalent peptide labeled with $^{99m}$Tc, and are incorporated herein by reference in their entirety. Pretargeting methods are also described in U.S. Ser. No. 09/823,746 (Hansen et al.) and Ser. No. 10/150,654 (Goldenberg et al.), and US Provisional Application filed Jan. 31, 2003, entitled "Methods and Compositions for Administration of Therapeutic and Diagnostic Agents, Atty Docket No. 018733/1103 (McBride et al.), which are all also incorporated herein by reference in their entirety. The delivery results in excellent tumor/normal tissue ratios for $^{125}$I and $^{99m}$Tc, thus showing the utility of two diagnostic radioisotopes. Any combination of known therapeutic agents or diagnostic agents can be used to label the antibodies and antibody fusion proteins. The binding specificity of the antibody component of the MAb conjugate, the efficacy of the therapeutic agent or diagnostic agent and the effector activity of the Fc portion of the antibody can be determined by standard testing of the conjugates.

A therapeutic or diagnostic agent can be attached at the hinge region of a reduced antibody component via disulfide bond formation. As an alternative, such peptides can be attached to the antibody component using a heterobifunctional crosslinker, such as N-succinyl 3-(2-pyridyldithio) proprionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same peptide that is bound to a thiol group, or the carbohydrate moiety can be used to bind a different peptide.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

The Fc region is absent if the antibody used as the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, all of which are incorporated in their entirety by reference. The engineered carbohydrate moiety is used to attach the therapeutic or diagnostic agent.

10. Pharmaceutically Acceptable Excipients

The humanized, chimeric and human anti-CD19 MAbs to be delivered to a subject can consist of the MAb alone, immunoconjugate, fusion protein, or can comprise one or more pharmaceutically suitable excipients, one or more additional ingredients, or some combination of these.

The immunoconjugate or naked antibody of the present invention can be formulated according to known methods to prepare pharmaceutically useful compositions, whereby the immunoconjugate or naked antibody are combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate or naked antibody of the present invention can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic or diagnostic conjugate or naked antibody. Control release preparations can be prepared through the use of polymers to complex or adsorb the immunoconjugate or naked antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate or antibody from such a matrix depends upon the molecular weight of the immunoconjugate or antibody, the amount of immunoconjugate, antibody within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate, antibody fusion proteins, or naked antibody may also be administered to a mammal subcutaneously or even by other parenteral routes. Moreover, the administration may be by continuous infusion or by single or multiple boluses. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of immunoconjugate, antibody fusion protein or naked antibody that is in the range of from about 1 mg/kg to 20 mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months. The dosage may be given through various parenteral routes, with appropriate adjustment of the dose and schedule.

For purposes of therapy, the immunoconjugate, fusion protein, or naked antibody is administered to a mammal in a therapeutically effective amount. A suitable subject for the present invention are usually a human, although a non-human animal subject is also contemplated. An antibody preparation is said to be administered in a "therapeutically effective amount" if the amount administered is physiologically significant. An agent is physiologically significant if its presence results in a detectable change in the physiology of a recipient mammal. In particular, an antibody preparation of the present invention is physiologically significant if its presence invokes an antitumor response or mitigates the signs and symptoms of an autoimmune disease state. A physiologically significant effect could also be the evocation of a humoral and/or cellular immune response in the recipient mammal.

11. Methods of Treatment

The present invention contemplates the use of naked anti-CD19 antibodies of the present invention as the primary composition for treatment of B cell disorders and other diseases. In particular, the compositions described herein are particularly useful for treatment of various autoimmune as well as indolent forms of B-cell lymphomas, aggressive forms of B-cell lymphomas, chronic lymphatic leukemias, acute lymphatic leukemias, and Waldenstrom's macroglobulinemia. For example, the humanized anti-CD19 antibody components and immunoconjugates can be used to treat both indolent and aggressive forms of non-Hodgkin's lymphoma.

As discussed above, the antibodies of the present invention are also suitable for diagnosis and treatment of various autoimmune diseases. Such diseases include acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, parmphigus vulgaris, Wegener's granulomatosis, membranous nephropathy, amyotrophic lateral sclerosis, tabes dorsalis, giant cell arteritis/polymyalgia, perniciousanemia, rapidly progressive glomerulonephritis, psoriasis, and fibrosing alveolitis. The most common treatments are corticosteroids and cytotoxic drugs, which can be very toxic. These drugs also suppress the entire immune system, can result in serious infection, and have adverse affects on the bone marrow, liver and kidneys. Other therapeutics that have been used to treat Class III autoimmune diseases to date have been directed against T-cells and macrophages. There is a need for more effective methods of treating autoimmune diseases, particularly Class ill autoimmune diseases.

The compositions for treatment contain at least one humanized, chimeric or human monoclonal anti-CD19 antibody alone or in combination with other antibodies, such as other humanized, chimeric, or human antibodies, therapeutic agents or immunomodulators. In particular, combination therapy with a fully human antibody is also contemplated and is produced by the methods as set forth above.

Naked or conjugated antibodies to the same or different epitope or antigen may be also be combined with one or more of the antibodies of the present invention. For example, a humanized, chimeric or human naked anti-CD19 antibody may be combined with another naked humanized, naked chimeric or naked human anti-CD19 (or with a naked CD20, CD22 or other B-cell lineage antibody), a humanized, chimeric or human naked anti-CD19 antibody may be combined with an anti-CD19 immunoconjugate, a naked anti-CD19 antibody may be combined with an anti-CD22 radioconjugate or an anti-CD22 naked antibody may be combined with a humanized, chimeric or human anti-CD19 antibody conjugated to an isotope, or one or more chemotherapeutic agents, cytokines, toxins or a combination thereof. A fusion protein of a humanized, chimeric or human CD19 antibody and a toxin or immunomodulator, or a fusion protein of at least two different B-cell antibodies (e.g., a CD19 and a CD22 MAb or a CD19 and a CD20 Mab) may also be used in this invention. Many different antibody combinations, targeting at least two different antigens associated with B-cell disorders, as listed already above, may be constructed, either as naked antibodies or as partly naked and partly conjugated with a therapeutic agent or immunomodulator, or merely in combination with another therapeutic agents, such as a cytotoxic drug or with radiation.

As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-I0, IL-12, IL-21 and IL-18), colony stimulating factors (e.g., granulocyte-colony stimulating factor (G-CSF) and granulocyte macrophage-colony stimulating factor (GM-CSF)), interferons (e.g., interferons-alpha, -beta and -gamma), the stem cell growth factor designated "S1 factor," erythropoietin and thrombopoietin. Examples of suitable immunomodulator moieties include IL-2, IL-6, IL-10, IL-12, IL-18, IL-21, interferon-, TNF-, and the like. Alternatively, subjects can receive naked anti-CD19 antibodies and a separately administered cytokine, which can be administered before, concurrently or after administration of the naked anti-CD19 antibodies. As discussed supra, the anti-CD19 antibody may also be conjugated to the immunomodulator. The immunomodulator may also be conjugated to a hybrid antibody consisting of one or more antibodies binding to different antigens.

Multimodal therapies of the present invention further include immunotherapy with naked anti-CD 19 antibodies supplemented with administration of antibodies that bind CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC1, Ia, HM1.24, HLA-DR (including the invariant chain), tenascin, VEGF, PIGF, ED-B fibronectin, an oncogene, an oncogene product, NCA 66a-d, necrosis antigens, Ii, IL-2, T101, TAC, IL-6, TRAIL-R1 (DR4) and TRAIL-R2 (DR5) antibodies in the form of naked antibodies, fusion proteins, or as immunoconjugates. These antibodies include polyclonal, monoclonal, chimeric, human or humanized antibodies that recognize at least one epitope on these antigenic determinants. Anti-CD 19 and anti-CD22 antibodies are known to those of skill in the art. See, for example, Ghetie et al., *Cancer Res.* 48:2610 (1988); Hekman et al., *Cancer Immunol. Immunother.* 32: 364 (1991); Longo, *Curr. Opin. Oncol.* 8:353 (1996) and U.S. Pat. Nos. 5,798,554 and 6,187,287, incorporated in their entirety by reference. Immunotherapy of autoimmune disorders with B-cell antibodies is described in the art. See, for example, WO0074718A1, which is incorporated herein by reference in its entirety.

In another form of multimodal therapy, subjects receive naked anti-CD19 antibodies, and/or immunoconjugates, in conjunction with standard cancer chemotherapy. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 202&-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate and bryostatin-1. Antisense bcl-2 oligonucleotide is also in clinical trials as a therapeutic for certain malignancies, including B-cell tumors. In a preferred multimodal therapy, both chemotherapeutic drugs and cytokines are co-administered with an antibody, immunoconjugate or fusion protein according to the present invention. The cytokines, chemotherapeutic drugs and antibody or immunoconjugate can be administered in any order, or together.

In a preferred embodiment, NHL is treated with 4 weekly infusions of the humanized anti-CD19 antibody at a dose of 200-400 mg/m$^2$ weekly for 4 consecutive weeks (iv over 2-8 hours), repeated as needed over next months/yrs. Also preferred, NHL is treated with 4 weekly infusions as above, but combined with epratuzumab (anti-CD22 humanized antibody) on the same days, at a dose of 360 mg/m2, given as iv infusion over 1 hour, either before, during or after the anti-CD19 monoclonal antibody infusion. Still preferred, NHL is treated with 4 weekly infusions of the anti-CD19 antibody as above, combined with one or more injections of CD22 MAb radiolabeled with a therapeutic isotope such as yttrium-90 (at dose of Y-90 between 5 and 35 mCi/meter-square as one or more injections over a period of weeks or months. CD19 MAb may also be combined, in similar regimens, with anti-CD20 Mabs, such as the hA20 humanized MAb (U.S. application Ser. No. 10/366,709, filed Feb. 14, 2003), whereby a weekly dose×4 weeks per cycle, with optional repeated cycles, is given of each antibody at an individual dose of 250 mg/m2 i. v. in combination. Either or both antibodies can also be given by s.c. injection, whereby a similar dose is given every other week, particularly for the therapy of patients with autoimmune disease.

In addition, a therapeutic composition of the present invention can contain a mixture or hybrid molecules of monoclonal naked anti-CD19 antibodies directed to different, non-blocking CD19 epitopes. Accordingly, the present invention contemplates therapeutic compositions comprising a mixture of monoclonal antiCD19 antibodies that bind at least two CD19 epitopes. Additionally, the therapeutic composition described herein may contain a mixture of anti-CD 19 antibodies with varying CDR sequences.

Although naked anti-CD 19 antibodies are the primary therapeutic compositions for treatment of B cell lymphoma and autoimmune diseases, the efficacy of such antibody therapy can be enhanced by supplementing the naked antibodies, with supplemental agents, such as immunomodulators, like interferons, including IFN-alpha, IFN-beta and IFN-gamma, interleukins including IL-1, IL-2, IL-6, IL-12, IL-15, IL-18, IL-21, and cytokines including G-CSF and GM-CSF. Accordingly, the CD19 antibodies can be combined not only with antibodies and cytokines, either as mixtures (given separately or in some predetermined dosing regiment) or as conjugates or fusion proteins to the anti-CD19 antibody, but also can be given as a combination with drugs. For example, the anti-CD19 antibody may be combined with CHOP as a 4-drug chemotherapy regimen. Additionally, a naked anti-CD 19 antibody may be combined with a naked anti-CD22 antibodies and/or naked anti-CD20 antibodies and CHOP or Fludarabine as a drug combination for NHL therapy. The supplemental therapeutic compositions can be administered before, concurrently or after administration of the anti-CD19 antibodies.

As discussed supra, the antibodies of the present invention can be used for treating B cell lymphoma and leukemia, and other B cell diseases or disorders. The antibodies may be used for treating any disease or syndrome which involves unwanted or undesirable B-cell activity or proliferation. For example, anti-CD19 antibodies can be used to treat B-cell related autoimmune diseases, including Class III autoimmune diseases such as immune-mediated thrombocytopenias, such as acute idiopathic thrombocytopenic purpura and chronic idiopathic thrombocytopenic purpura, dermatomyositis, Sjogren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis. The antibodies can also be used to treat B-cell diseases such as graft versus host disease, or for transplant immunosuppressive therapy.

Anti-CD19 antibodies may also induce apoptosis in cells expressing the CD19 antigen. Evidence of this induction is supported in the literature. For example, it was demonstrated that apoptosis could be induced using lymphoid cells that have Fc-receptors reactive with the IgG1-Fc of CD19 MAbs that crosslinked. See Shan et al., *Cancer Immunol. Immunother.* 48(12):673-683 (2000). Further, it was reported that aggregates of a chimeric CD19 MAb, i.e., homopolymers, induced apoptosis. See Ghetie et al., *Blood* 97(5): 1392-1398 (2000) and Ghetie et al., *Proc. Natl. Acad. Sci USA* 94(14): 7509-7514 (1997). Enhancement of the pro-apoptotic activity of the antibodies may be achieved by simultaneous use of a pro-apoptotic agent, such as an agent that inhibits the activity of one or more members of the anti-apoptosis gene family bcl-2. Antisense and RNAi agents are particularly useful in this regard and can be directed to B cells by conjugation with CD 19 antibodies as described herein.

Antibodies specific to the CD19 surface antigen of B cells can be injected into a mammalian subject, which then bind to the CD19 cell surface antigen of both normal and malignant B cells. A mammalian subject includes humans and domestic animals, including pets, such as dogs and cats. The anti-CD19 MAbs of the present invention, i.e., humanized, chimeric, human, caninized and felinized, and even murine anti-CD19 MAbs, can be used to treat the non-human maminalian subjects when there is a species crossreactivity for the CD 19 antigen. See Examples 10 and 11, below. The murine MAbs, which are immunogenic in humans, are usually less immunogenic in non-human mammalian subjects. The anti-CD19 antibody bound to the CD19 surface antigen leads to the destruction and depletion of neoplastic B cells. Because both normal and malignant B cells express the CD19 antigen, the anti-CD19 antibody will result in B cell death. However, only normal B cells will repopulate and the malignant B cells will be eradicated or significantly reduced. Additionally, chemical agents or radioactive labels having the potential to destroy the tumor can be conjugated to the anti-CD 19 antibody such that the agent is specifically targeted to the neoplastic B cells.

12. Expression Vectors

The DNA sequence encoding a humanized, chimeric or human anti-CD19 MAb can be recombinantly engineered into a variety of known host vectors that provide for replication of the nucleic acid. These vectors can be designed, using known methods, to contain the elements necessary for directing transcription, translation, or both, of the nucleic acid in a cell to which it is delivered. Known methodology can be used to generate expression constructs the have a protein-coding sequence operably linked with appropriate transcriptional/translational control signals. These methods include in vitro recombinant DNA techniques and synthetic techniques. For example, see Sambrook et al., 1989, MOLECULAR CLONING: A LABORATORY MANUAL, Cold Spring Harbor Laboratory (New York); Ausubel et al., 1997, CURRENT PROTOCOLS IN MOLECULAR BIOLOGY, John Wiley & Sons (New York). Also provided for in this invention is the delivery of a polynucleotide not associated with a vector.

Vectors suitable for use in the instant invention can be viral or non-viral. Particular examples of viral vectors include adenovirus, AAV, herpes simplex virus, lentivirus, and retrovirus vectors. An example of a non-viral vector is a plasmid. In a preferred embodiment, the vector is a plasmid.

An expression vector, as described herein, is a polynucleotide comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

Preferably, the expression vector of the instant invention comprises the DNA sequence encoding a humanized, chimeric or human anti-CD19 MAb, which includes both the heavy and the light chain variable and constant regions. However, two expression vectors may be used, with one comprising the heavy chain variable and constant regions and the other comprising the light chain variable and constant regions. Still preferred, the expression vector further comprises a promoter, a DNA sequence encoding a secretion signal peptide, a genomic sequence encoding a human IgG1 heavy chain constant region, an Ig enhancer element and at least one DNA sequence encoding a selection marker.

Also contemplated herein is a method for expressing a humanized anti-CD19 MAb, comprising (i) linearizing at least one expression vector comprising a DNA sequence encoding a humanized, chimeric, or human anti-CD19 MAb, (ii) transfecting mammalian cells with at least one of said linearized vector, (iii) selecting transfected cells which express a marker gene, and (iv) identifying the cells secreting the humanized anti-CD 19 MAb from the transfected cells.

13. Methods of Making Anti-CD19 Antibodies

In general, the $V_K$ (variable light chain) and $V_H$ (variable heavy chain) sequences for an anti-CD19 MAb can be obtained by a variety of molecular cloning procedures, such as RT-PCR, 5'-RACE, and cDNA library screening. Specifically, the V genes of an anti-CD19 MAb can be cloned by PCR amplification from a cell that expresses a murine or chimeric anti-CD19 MAb, sequenced. To confirm their authenticity, the cloned $V_L$ and $V_H$ genes can be expressed in cell culture as a chimeric Ab as described by Orlandi et al., (Proc. Natl. Acad. Sci., USA, 86: 3833 (1989)) which is incorporated by reference. Based on the V gene sequences, a humanized anti-CD19 MAb can then be designed and constructed as described by Leung et al. (Mol. Immunol., 32: 1413 (1995)), which is incorporated by reference. cDNA can be prepared from any known hybridoma line or transfected cell line producing a murine or chimeric anti-CD 19 MAb by general molecular cloning techniques (Sambrook et al., Molecular Cloning, A laboratory manual, 2nd Ed (1989)). The $V_K$ sequence for the MAb may be amplified using the primers VK1BACK and VK1FOR (Orlandi et al., 1989) or the extended primer set described by Leung et al. (BioTechniques, 15: 286 (1993)), which is incorporated by reference, while $V_H$ sequences can be amplified using the primer pair VH1BACK/VH1FOR (Orlandi et al., 1989 above), or the primers annealing to the constant region of murine IgG described by Leung et al. (Hybridoma, 13:469 (1994), which is incorporated by reference. The PCR reaction mixtures containing 10 μl of the first strand cDNA product, 10 μl of 10×PCR buffer [500 mM KCl, 100 mM Tris-HCl (pH 8.3), 15 mM $MgCl_2$, and 0.01% (w/v) gelatin] (Perkin Elmer Cetus, Norwalk, Conn.), 250 μM of each dNTP, 200 nM of the primers, and 5 units of Taq DNA polymerase (Perkin Elmer Cetus) can be subjected to 30 cycles of PCR. Each PCR cycle preferably consists of denaturation at 94 C for 1 min, annealing at 50 C for 1.5 min, and polymerization at 72 C for 1.5 min. Amplified $V_K$ and VH fragments can be purified on 2% agarose (BioRad, Richmond, Calif.). Similarly, the humanized V genes can be constructed by a combination of long oligonucleotide template syntheses and PCR amplification as described by Leung et al. (Mol. Immunol., 32: 1413 (1995)). See Example 3 for a method for the synthesis of an oligo A and an oligo B on an automated RNA/DNA synthesizer (Applied Biosystems, Foster City, Calif.) for use in constructing humanized V genes.

PCR products for $V_K$ can be subcloned into a staging vector, such as a pBR327-based staging vector, VKpBR, that contains an Ig promoter, a signal peptide sequence and convenient restriction sites to facilitate in-frame ligation of the $V_{KK}$ PCR products. PCR products for $V_H$ can be subcloned into a similar staging vector, such as the pBluescript-based VHpBS. Individual clones containing the respective PCR products may be sequenced by, for example, the method of Sanger et al. (Proc. Natl. Acad. Sci., USA, 74: 5463 (1977)), which is incorporated by reference.

The DNA sequences described herein are to be taken as including all alleles, mutants and variants thereof, whether occurring naturally or induced.

The expression cassettes containing the $V_K$ and VH, together with the promoter and signal peptide sequences can be excised from YKpBR and VHpBS, respectively, by double restriction digestion as HindIII-BamHI fragments. The $V_K$ and VH expression cassettes can then be ligated into appropriate expression vectors, such as pKh and pG1g, respectively (Leung et al., Hybridoma, 13:469 (1994)). The expression vectors can be co-transfected into an appropriate cell, e.g., myeloma Sp2/0-Ag14 (ATCC, VA), colonies selected for hygromycin resistance, and supernatant fluids monitored for production of a chimeric or humanized anti-CD19 MAb by, for example, an ELISA assay, as described below. Alternately, the $V_K$ and VH expression cassettes can be assembled in the modified staging vectors, YKpBR2 and VHpBS2, excised as XbaI/BamHI and XhoI/BamHI fragments, respectively, and subcloned into a single expression vector, such as pdHL2, as described by Gilles et al. (J. Immunol. Methods 125:191 (1989) and also shown in Losman et al., Cancer, 80:2660 (1997)) for the expression in Sp2/0-Ag14 cells. Another vector that is useful in the present invention is the GS vector, as described in Barnes et al., Cytotechnology 32: 109-123 (2000), which is preferably expressed in the NS0 cell line and CHO cells. Other appropriate mammalian expression systems are described in Werner et al., Arzneim.-Forsch./ Drug Res. 48(II), Nr. 8, 870-880 (1998).

Co-transfection and assay for antibody secreting clones by ELISA, can be carried out as follows. About 10 μg of VKpKh (light chain expression vector) and 20 μg of VHpG1g (heavy chain expression vector) can be used for the transfection of 5×10⁶ SP2/0 myeloma cells by electroporation (BioRad, Richmond, Calif.) according to Co et al., *J. Immunol.*, 148: 1149 (1992) which is incorporated by reference. Following transfection, cells may be grown in 96-well microtiter plates in complete HSFM medium (Life Technologies, Inc., Grand Island, N.Y.) at 37ΨC, 5% C02. The selection process can be initiated after two days by the addition of hygromycin selection medium (Calbiochem, San Diego, Calif.) at a final concentration of 500 units/ml of hygromycin. Colonies typically emerge 2-3 weeks post-electroporation. The cultures can then be expanded for further analysis.

Transfectoma clones that are positive for the secretion of chimeric or humanized heavy chain can be identified by ELISA assay. Briefly, supernatant samples (~100 μl) from transfectoma cultures are added in triplicate to ELISA microtiter plates precoated with goat anti-human (GAH)-IgG, F(ab')₂ fragment-specific antibody (Jackson ImmunoResearch, West Grove, Pa.). Plates are incubated for 1 h at room temperature. Unbound proteins are removed by washing three times with wash buffer (PBS containing 0.05% polysorbate 20). Horseradish peroxidase (HRP) conjugated GAH-IgG, Fc fragment-specific antibodies (Jackson ImmunoResearch) are added to the wells, (100 μl of antibody stock diluted×10⁴, supplemented with the unconjugated antibody to a final concentration of 1.0 μg/ml). Following an incubation of 1 h, the plates are washed, typically three times. A reaction solution, [100 μl, containing 167 μg of orthophenylene-diamine (OPD) (Sigma, St. Louis, Mo.), 0.025% hydrogen peroxide in PBS], is added to the wells. Color is allowed to develop in the dark for 30 minutes. The reaction is stopped by the addition of 50 μl of 4 N HCl solution into each well before measuring absorbance at 490 nm in an automated ELISA reader (Bio-Tek instruments, Winooski, Vt.). Bound chimeric antibodies are than determined relative to an irrelevant chimeric antibody standard (obtainable from Scotgen, Ltd., Edinburg, Scotland).

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2 μm membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 μl of 3 M Tris (pH 8.6), and protein concentrations determined from the absorbance at 280/260 nm. Peak fractions are pooled, dialyzed against PBS, and the antibody concentrated, for example, with the Centricon 30 (Amicon, Beverly, Mass.). The antibody concentration is determined by ELISA, as before, and its concentration adjusted to about 1 mg/ml using PBS. Sodium azide, 0.01% (w/v), is conveniently added to the sample as preservative.

The following are the nucleotide sequences of the primers used to prepare the anti-CD 19 antibodies:

```
hA19VKA                                 (SEQ ID NO:24)
5'-ATCACTTGTA AGGCCAGCCA AAGTGTTGAT TATGATGGTG
ATAGTTATTT GAACTGGTAC CAGCAGATTC CAGGGAAAGC
ACCTAAATTG TTGATCTACG ATGCTTCGAA TCTAGTTTCT
GGTATC-3' hA19VKB                                 (SEQ ID NO:25)
5'-TGCTGACAGT GATATGTTGC AATGTCTTCT GGTTGAAGAG
AGCTGATGGT GAAAGTGTAA TCTGTCCCAG ATCCGCTGCC
AGAGAATCGA GGAGGGATAC CAGAAACTAG ATTCGAAGCA
TCGTA-3' hA19VKBack                              (SEQ ID NO:26)
5'-TCCGACATCC AGCTGACCCA GTCTCCATCA TCTCTGAGCG
CATCTGTTGG AGATAGGGTC ACTATCACTT GTAAGGCCAG
CCAAAG-3' hA19VKFor                               (SEQ ID NO:27)
5'-GCTCCTTGAG ATCTGTAGCT TGGTCCCTCC ACCGAACGTC
CACGGATCTT CAGTACTTTG CTGACAGTGA TATGTTGCAA-3' hA19VHA                                 (SEQ ID NO:28)
5'-CTGGCTACGC TTTCAGTAGC TACTGGATGA ACTGGGTGAG
GCAGAGGCCT GGACAGGGTC TTGAGTGGAT TGGACAGATT
TGGCCTGGAG ATGGTGATAC TAACTACAAT GGAAAGTTCA
AGGGGCGCGC CACTATT-3' hA19VHB                                 (SEQ ID NO:29)
5'-CGTAGTCTCC CGTCTTGCAC AAGAATAGAA CGCTGTGTCC
TCAGATCGTA GGCTGCTGAG TTCCATGTAG GCTGTATTAG
TGGATTCGTC GGCAGTAATA GTGGCGCGCC CCTTGAACTT
TCCATTGTA-3' hA19VHBack                              (SEQ ID NO:30)
5'-CAGGTCCAAC TGCAGCAATC AGGGGCTGAA GTCAAGAAAC
CTGGGTCATCG GTGAAGGTCTC CTGCAAGGCT TCTGGCTACG
CTTTCAGTAG C-3' hA19VHFor                               (SEQ ID NO:31)
5'-TGAGGAGACG GTGACCGTGG TCCCTTGGCC CCAGTAGTCC
ATAGCATAGT AATAACGGCC TACCGTCGTA GTCTCCCGTC
TTGCACAAG-3'
```

The invention is further described by reference to the following examples, which are provided for illustration only. The invention is not limited to the examples but rather includes all variations that are evident from the teachings provided herein.

EXAMPLE 1

Construction of a Humanized Anti-CD19 Antibody

A chimeric A19 (cA19) antibody was constructed and expressed in Sp2/0 cell. The Vk (SEQ ID NO:6) and VH (SEQ ID NO:9) sequences of cA19 are shown in FIG. 1. The cA19 antibody was shown to bound to CD19⁺ human lymphoma cell lines, such as Raji, Daudi, and Ramos. The Ag-binding specificity of purified cA19 was evaluated by a cell surface competitive binding assay against other anti-CD19 antibodies, e.g. B4 (Coulter) and BU12 (Chembiochem). Briefly, varying concentrations of cA19 was incubated with Raji cells in the presence of a constant amount of an I-125 radiolabeled anti-CD19 antibody for 1 h. After washing to remove the unbound antibodies, the cell surface-bound radio labeled antibody was quatitated by counting the cell pellets in a gamma counter. As shown in FIG. 2, cA19 competed with BU12 (Chembiochem) for cell surface binding, indicating these antibodies share similar or overlap epitopes of the CD19 molecule.

The light chain and heavy chain variable region sequences encoding the humanized anti-hCD19 antibody (hA19) were designed and constructed. Comparison of the variable (V) region framework (FR) sequences of the cA19 (FIGS. 1A;

SEQ ID NO:1 and SEQ ID NO:2; and 1B; SEQ ID NO:3 and SEQ ID NO:4) to registered human antibodies in the Kabat database showed that the FRs of cA19 $V_K$ (SEQ ID NO:6) exhibited the highest degree of sequence homology to that of the human antibody REI ($V_K$; SEQ ID NO:5), while the VH sequence was most closely related with that of EU (VH; SEQ ID NO:5). The VH FR4 (SEQ ID NO:11) sequence of the human antibody, NEWM, however, was better aligned with that of cA19 and used to replace the EU FR4 sequence for the humanization of the A19 heavy chain (FIG. 3B). Therefore, human REI framework sequences were used for VK (FIG. 3A), and a combination of EU and NEWM framework sequences were used for VH (FIG. 3B). There are a number of amino acid changes in each chain outside of the CDR regions when compared to the starting human antibody frameworks. The heavy chain of hA19, hA19VH (SEQ ID NO:10) contains nine changes from the human EU and NEWM frameworks (FIG. 3B). The light chain of Ha19, hA19VK (SEQ ID NO:13), contains nine amino acid changes from the REI framework (FIG. 2A). These residues are 4L, 39I, 58I, 60P, 87H, 100G, and 107K of $V_K$ and 5Q, 27Y, 28A, 40R, 91S, 94R, 107T, and 108T of VH. The DNA and amino acid sequences of hA19 $V_K$ (SEQ ID NO:12 and SEQ ID NO:13) and VH (SEQ ID NO:14 and SEQ ID NO:15) are shown in FIGS. 4A and 4B, respectively.

EXAMPLE 2

Method of hA19 Antibody Construction

To engineer the CDR-grafted Ha19VH and $V_K$ genes, a modified strategy as described by Leung et al.[3] was used to construct the designed $V_K$ and VH genes for hA19 using a combination of long oligonucleotide syntheses and PCR. Briefly, two long synthetic oligonucleotides (ca. 130 mer in length) representing the 5'-(sense strand, designated as A) and 3'-half (anti-sense strand, designated as B) of a V sequence are used as the templates in a PCR reaction. The 3'-terminal sequences of the long oligonucleotides A and B are designed to be overlap and complementary to each other. PCR is initiated by annealing of the 3'-termini of A and B to form a short double strand DNA flanked by the rest of long oligonucleotides (single strand). Each annealed end serves as a primer for the replication of the single stranded DNA, resulting in elongation of A and B to form the double-strand DNA. In the presence of two short oligonucleotide primers, V gene segment is generated by PCR amplification of the double strand DNA.

Heavy Chain

For the construction of hA19 VH domain, the long oligonucleotides, hA19VHA (126-mer) and hA19VHB (128-mer) were synthesized on an automated DNA synthesizer (Applied Biosystem). hA19VHA represents nt 74 to 126 of the hA19 VH domain, and hA19VHB represents the minus strand of the hA19VH domain complementary to nt 178 to 306. The 3'-terminal sequences (33 nt residues) of hA19VHA and VHB are complementary to each other. A minimal amount of hA19VHA and VHB (determined empirically) was amplified in the presence of 10 µL of 10×PCR Buffer (500 mM KCL, 100 mM Tris. HCL buffer, pH 8.3, 15 mM MgCl.sub.2), 2 µmol of hA19VH Back (5'-CAGGTCCAAC TGCAGCAATC AGGGGCTGAA GTCAAGAAAC CTGGGT-CATCG GTGAAGGTCTC CTGCAAGGCT TCTGGC-TACG CTTTCAGTAG C-3': SEQ ID NO:30) and hA19VHF or (5'-TGAGGAGACG GTGACCGTGG TCCCTTGGCC CCAGTAGTCC ATAGCATAGT AATAACGGCC TAC-CGTCGTA GTCTCCCGTC TTGCACAAG-3': SEQ ID NO:31), and 2.5 units of Taq DNA polymerase (Perkin Elmer Cetus, Norwalk, Conn.). The underlined portions are the restriction sites for subcloning as shown in FIG. 4B. This reaction mixture was subjected to three cycles of polymerase chain reaction (PCR) consisting of denaturation at 94° C. for 1 minute, annealing at 45° C. for 1 minute, and polymerization at 72° C. for 1.5 minutes. This procedure was followed by 27 cycles of PCR reaction consisting of denaturation at 94 C. for 1 minute, annealing at 55° C. for 1 minute, and polymerization at 72° C. for 1 minute. The resulting DNA fragment showed an expected molecular size of 350 in agarose gel electrophoresis. The double-stranded PCR-amplified product for hA19VH was gel-purified, restriction-digested with PstI and BstEII restriction enzymes and cloned into the complementary PstI/BstEII restriction sites of the heavy chain staging vector, VHpBS2, in which the VH sequence was fully assembled with the DNA sequence encoding the translation initiation codon and a secretion signal peptide in-frame ligated at the 5'-end and an intron sequence at the 3'-end. VHpBS2 is a modified staging vector of VHpBS (Leung et al., Hybridoma, 13:469 (1994)), into which a XhoI restriction site was introduced at sixteen bases upstream of the translation initiation codon to facilitate the next subcloning step. The assembled VH gene was subcloned as a XhoI-BamHI restriction fragment into the expression vector, pdHL2, which contains the expression cassettes for both human IgG heavy and light chains under the control of IgH enhancer and $MT_1$ promoter, as well as a mouse dhfr gene as a marker for selection and amplification (FIG. 4B). Since the heavy chain region of pdHL2 lacks a BamHI restriction site, this ligation requires use of a linker to provide a bridge between the BamHI site of the variable chain and the HindIII site present in the pdHL2 vector. The resulting expression vectors were designated as hA19VHpdHL2.

For constructing the full length DNA of the humanized $V_K$ sequence, hA19VKA (126-mer, represents nt 61 to 186 of the hA19 $V_K$ domain) and hA19VKB (124-mer, represents the minus strand of the hA19 $V_K$ domain complementary to nt 157 to 281) were synthesized as described above. hA19VKA and VKB were amplified by two short oligonucleotides hA19VK Back (5'- CAGGTCCAAC TGCAGCAATC AGGGGCTGAA GTCAAGAAAC CTGGGTCATCG GTGAAGGTCTC CTGCAAGGCT TCTGGCTACG CTTTCAGTAG C-3': SEQ ID NO:30') and hA19VK For (5'-TGAGGAGACG GTGACCGTGG TCCCTTGGCC CCAGTAGTCC ATAGCATAGT AATAACGGCC TAC-CGTCGTA GTCTCCCGTC TTGCACAAG-3': SEQ ID NO:31) as described above. The underlined portions are restriction sites for subcloning as described below. Gel-purified PCR products for hA19 $V_K$ were restriction-digested with PvuII and BglII and cloned into the complementary PvuII/BclI sites of the light chain staging vector, VKpBR2. VKpBR2 is a modified staging vector of VKpBR (Leung et at, Hybridoma, 13:469 (1994)), into which a XbaI restriction site was introduced at sixteen bases upstream of the translation initiation codon. The assembled $V_K$ genes were subcloned as XbaI-BamHI restriction fragments into the expression vector containing the VH sequence, hA19VHpdHL2. The resulting expression vectors were designated as hA19pdHL2.

EXAMPLE 3

Transfection and Expression of hA19 Antibodies

Approximately 30 g of the expression vectors for hA19 was linearized by digestion with SalI and transfected into Sp2/0-Ag14 cells by electroporation (450V and 25 J-µF). The transfected cells were plated into 96-well plates for 2 days and then selected for drug-resistance by adding MTX into the medium at a final concentration of 0.075 μM. MTX-resistant colonies emerged in the wells 2-3 weeks. Supernatants from colonies surviving selection were screened for human Ab secretion by ELISA assay. Briefly, 100 μl supernatants were added into the wells of a microtiter plate precoated with GAH-IgG, F(ab')$_2$ fragment-specific Ab and incubated for 1 h at room temperature. Unbound proteins were removed by washing three times with wash buffer (PBS containing 0.05% polysorbate 20). HRP-conjugated GAH-IgG, Fc fragment-specific Ab was added to the wells. Following an incubation of 1 h, the plate was washed. The bound HRP-conjugated Ab was revealed by reading A490 nm after the addition of a substrate solution containing 4 mM OPD and 0.04% $H_2O_2$. Positive cell clones were expanded and hB43 were purified from cell culture supernatant by affinity chromatography on a Protein A column.

EXAMPLE 4

Determination of the Antigen-Binding Specificity and Affinity of antiCD19 Antibodies The Ag-binding specificity of cA19 and hA190 purified by affinity chromatography on a Protein A column were evaluated and compared by a cell surface competitive binding assay. Briefly, a constant amount (100,000 cpm, ~10 μCi/μg) of $^{125}$I-labeled cA19 or hA19 was incubated with Raji cells in the presence of varying concentrations (0.2-700 nM) of cA19 or hA19 at 4° C. for 1-2 h. Unbound Abs were removed by washing the cells in PBS. The radioactivity associated with cells was determined after washing. As shown in FIG. 2, the purified hA19 competed with $^{125}$I-labeled cA19 for cell surface binding and vice versa, indicating the apparent binding avidities are comparable between these two Abs.

The antigen-binding affinity (avidity} constant of hA19 was determined by direct cell surface binding assay of the radiolabeled Ab and Scatchard plot analysis, in comparison to that of cA19. Briefly, hA19 and cA19 were labeled with $^{125}$I by the chloramines-T method. Varying amounts of either $^{125}$I-hA19 or $^{125}$I-cA19 were incubated with 2×10$^5$ Raji cells at 4° C. for 2 h and unbound antibodies were removed by washing. The cell-associated radioactivity was counted and Scatchard plot analysis was performed to determine the maximum number of hA19 and cA19 binding sites per cell and the apparent dissociation constants of the equilibrium binding. As shown in FIG. 3, hA19 showed virtually same binding affinity as cA19. The apparent dissociation constant values for these two antibodies were calculated to be 1.1 and 1.2 nM, respectively.

EXAMPLE 5

Therapy of Non-Hodgkin's Lymphoma

A patient with indolent, follicular-cell NHL relapses after chemotherapy including dexamethasone, and has disease in the chest (para-aortic lymph nodes), an enlarged and involved spleen, and enlarged cervical lymph nodes. The patient is given a course of 300 mg/m$^2$ each of humanized CD19 MAb of this invention combined with humanized CD20 MAb (hA20) sequentially on the same day by i.v. infusion, weekly for 4 weeks, each time being premedicated with Tylenol® and Benadryl® according to standard, published doses for suppressing infusion-related reactions. Four weeks later, the patient returns for the first follow-up examination and the only observation is that some of the palpable lymph nodes feel softer. Upon returning 3 months following the first therapy cycle, the patient's chest disease appears to have become reduced by 40% on CT scan, the spleen is about half the pre-therapy size, and the cervical lymph nodes are almost gone. The patient is then given a retreatment cycle, and another three months later appears to have a normal-sized spleen, no cervical lymph nodes palpable or measurable on CT scan, and only a small, 1.5-cm lesion in the chest. The patient continues to appear almost free-of disease for another 4 months.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All of the publications and patent applications and patents cited in this specification are herein incorporated in their entirety by reference.

The invention claimed is:

1. A method of treating a B-cell disease in a subject comprising administering to a subject with a B-cell disease selected from lymphoma, leukemia or autoimmune disease, wherein the B-cells associated with the B-cell disease express CD19 antigen, a therapeutically effective amount of a humanized anti-CD19 antibody or an antigen-binding fragment thereof, wherein the antibody or antigen-binding fragment thereof comprises the amino acid sequence of hA19Vk SEQ ID NO:7 and hA19VH SEQ ID NO:10.

2. The method of claim 1, wherein the antibody or antigen-binding fragment thereof induces apoptosis of the B-cells that express CD19 antigen.

3. The method of claim 1, wherein said B-cell disease is selected from the group consisting of B cell lymphoma, non-Hodgkin's lymphoma, chronic lymphocytic leukemia and acute lymphocytic leukemia.

4. The method of claim 1, further comprising administering to said subject concurrently or sequentially a therapeutically effective amount of at least one humanized, chimeric, human or murine Mab.

5. The method of claim 1, further comprising administering to said subject concurrently or sequentially a therapeutically effective amount of at least one therapeutic agent.

6. The method of claim 5, wherein the therapeutic agent is conjugated to the anti-CD19 antibody or antigen-binding fragment thereof and is administered concurrently.

7. The method of claim 5, wherein said therapeutic agent comprises a cytotoxic agent, or a radioactive label.

8. The method of claim 1, wherein the anti-CD19 antibody or antigen-binding fragment thereof is administered as part of a bispecific or multispecific antibody or antigen-binding fragment thereof, the multispecific or bispecific antibody or antigen-binding fragment thereof containing at least one other antibody or antigen-binding fragment thereof.

9. The method of claim 8, further comprising administering to said subject concurrently or sequentially a therapeutically effective amount of at least one therapeutic agent.

10. The method of claim 7, wherein said cytotoxic agent is a drug or a toxin.

11. The method of claim 5, wherein said therapeutic agent is selected from the group consisting of erythropoietin, thrombopoietin, tumor necrosis factor (TNF), an interleukin (IL), granulocyte-colony stimulating factor (G-CSF), granulocyte macrophage-colony stimulating factor (GM-CSF)), interferon-alpha, interferon-beta, interferon-gamma, and stem cell growth factor S1 factor.

12. The method of claim 1, wherein said subject is a human.

13. The method of claim 5, wherein the therapeutic agent is a chemotherapeutic agent selected from the group consisting of vinca alkaloids, anthracyclines, epidophyllotoxins, taxanes, antimetabolites, alkylating agents, antibiotics, COX-2 inhibitors, antimitotics, doxorubicin, methotrexate, taxol, CPT-11, camptothecans, proteosome inhibitors, thalidomide, nitrogen mustards, alkyl sulfonates, nitrosoureas, triazenes, folic acid analogs, pyrimidine analogs, purine analogs and platinum coordina 14. A method of inducing apoptosis in cells expressing the CD19 antigen comprising exposing cells expressing the CD19 antigen to a humanized anti-CD19 antibody or an antigen-binding fragment thereof, wherein the antibody or antigen-binding fragment thereof comprises the amino acid sequence of hA19Vk SEQ ID NO:7 and hA19VH SEQ ID NO:10.

15. A method of inducing apoptosis in cells expressing the CD19 antigen, wherein the cells expressing the CD19 antigen are in a subject, comprising administering to the subject a humanized anti-CD19 antibody or an antigen-binding fragment thereof, wherein the antibody or antigen-binding fragment thereof comprises the sequence of hA19Vk SEQ ID NO:7 and hA19VH SEQ ID NO:10.

16. The method of claim 15, wherein the subject has a B-cell disease selected from the group onsisting of a B-cell lymphoma, leukemia and autoimmune disease and the B-cells associated with the B-cell disease express CD19 antigen.

17. The method of claim 16, wherein the B-cell disease is non-Hodgkin's lymphoma, chronic lyitphocytic leukemia or acute lymphocytic leukemia.

18. The method of claim 16, further comprising administering to said subject concurrently or sequentially a therapeutically effective amount of at least one humanized, chimeric, human or murine Mab.

19. The method of claim 16, further comprising administering to said subject concurrently or sequentially a therapeutically effective amount of at least one therapeutic agent.

20. The method of claim 19, wherein the therapeutic agent is conjugated to the anti-CD19 antibody or antigen-binding fragment thereof and is administered concurrently.

21. The method of claim 20, wherein said therapeutic agent comprises a cytotoxic agents or a radioactive label.

* * * * *

UNITED STATES PATENT AND TRADEMARK OFFICE
CERTIFICATE OF CORRECTION

PATENT NO. : 7,462,352 B2 Page 1 of 1
APPLICATION NO. : 11/445410
DATED : December 9, 2008
INVENTOR(S) : Hans J. Hansen et al.

It is certified that error appears in the above-identified patent and that said Letters Patent is hereby corrected as shown below:

Col. 60, claim should read as follows:
17. The method of claim 16, wherein the B-cell disease is non-Hodgkin's lymphoma, chronic lymphocytic leukemia or acute lymphocytic leukemia. (correct spelling of lymphocytic)

Signed and Sealed this

Twentieth Day of January, 2009

JON W. DUDAS
*Director of the United States Patent and Trademark Office*

UNITED STATES PATENT AND TRADEMARK OFFICE
CERTIFICATE OF CORRECTION

PATENT NO. : 7,462,352 B2  Page 1 of 1
APPLICATION NO. : 11/445410
DATED : December 9, 2008
INVENTOR(S) : Hans J. Hansen et al.

It is certified that error appears in the above-identified patent and that said Letters Patent is hereby corrected as shown below:

Col. 60, line 65-67, claim 17, should read as follows:
17. The method of claim 16, wherein the B-cell disease is non-Hodgkin's lymphoma, chronic lymphocytic leukemia or acute lymphocytic leukemia. (correct spelling of lymphocytic)

This certificate supersedes the Certificate of Correction issued January 20, 2009.

Signed and Sealed this

Seventeenth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,462,352 B2
APPLICATION NO. : 11/445410
DATED : December 9, 2008
INVENTOR(S) : Hans J. Hansen et al.

It is certified that error appears in the above-identified patent and that said Letters Patent is hereby corrected as shown below:

Title Page; Item (54) Title:
Change "TREATNG" to --TREATING--

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,462,352 B2  Page 1 of 1
APPLICATION NO. : 11/445410
DATED : December 9, 2008
INVENTOR(S) : Hans J. Hansen et al.

It is certified that error appears in the above-identified patent and that said Letters Patent is hereby corrected as shown below:

Title Page, Item (54) and at Column 1, line 1, Title:
Change "TREATNG" to --TREATING--

This certificate supersedes the Certificate of Correction issued April 13, 2010.

Signed and Sealed this

Thirteenth Day of July, 2010

David J. Kappos
*Director of the United States Patent and Trademark Office*

SEQUENCE LISTING

```
<160> NUMBER OF SEQ ID NOS: 31

<210> SEQ ID NO 1
<211> LENGTH: 336
<212> TYPE: DNA
<213> ORGANISM: Artificial Sequence
<220> FEATURE:
<223> OTHER INFORMATION: Description of Artificial Sequence: Synthetic
      anti-CD19 antibody, cA19
<220> FEATURE:
<221> NAME/KEY: CDS
<222> LOCATION: (1)..(336)

<400> SEQUENCE: 1 gac atc cag ctg acc cag tct cca gct tct ttg gct gtg tct cta ggg      48
Asp Ile Gln Leu Thr Gln Ser Pro Ala Ser Leu Ala Val Ser Leu Gly
  1               5                  10                  15 cag agg gcc acc atc tcc tgc aag gcc agc caa agt gtt gat tat gat      96
```

```
Gln Arg Ala Thr Ile Ser Cys Lys Ala Ser Gln Ser Val Asp Tyr Asp
            20                  25                  30 ggt gat agt tat ttg aac tgg tac caa cag att cca gga cag cca ccc        144
Gly Asp Ser Tyr Leu Asn Trp Tyr Gln Gln Ile Pro Gly Gln Pro Pro
        35                  40                  45 aaa ctc ctc atc tat gat gca tcc aat cta gtt tct ggc atc cca ccc        192
Lys Leu Leu Ile Tyr Asp Ala Ser Asn Leu Val Ser Gly Ile Pro Pro
    50                  55                  60 agg ttt agt ggc agt ggg tct ggg aca gac ttc acc ctc aac atc cat        240
Arg Phe Ser Gly Ser Gly Ser Gly Thr Asp Phe Thr Leu Asn Ile His
 65                 70                  75                  80 cct gtg gag aag gtg gat gct gca acc tat cac tgt cag caa agt act        288
Pro Val Glu Lys Val Asp Ala Ala Thr Tyr His Cys Gln Gln Ser Thr
                85                  90                  95 gaa gat ccg tgg acg ttc ggt gga ggg acc aag ctg gag atc aaa cgt        336
Glu Asp Pro Trp Thr Phe Gly Gly Gly Thr Lys Leu Glu Ile Lys Arg
            100                 105                 110

<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      anti-CD19 antibody, cA19

<400> SEQUENCE: 2

Asp Ile Gln Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
 65                 70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

<210> SEQ ID NO 3
<211> LENGTH: 372
<212> TYPE: DNA
<213> ORGANISM: Artificial Sequence
<220> FEATURE:
<223> OTHER INFORMATION: Description of Artificial Sequence: Synthetic
      anti-CD19 antibody, cA19
<220> FEATURE:
<221> NAME/KEY: CDS
<222> LOCATION: (1)..(372)

<400> SEQUENCE: 3 cag gtc caa ctg cag gag tct ggg gct gag ctg gtg agg cct ggg tcc         48
Gln Val Gln Leu Gln Glu Ser Gly Ala Glu Leu Val Arg Pro Gly Ser
 1               5                  10                  15 tca gtg aag att tcc tgc aag gct tct ggt tat gca ttc agt agc tac         96
Ser Val Lys Ile Ser Cys Lys Ala Ser Gly Tyr Ala Phe Ser Ser Tyr
            20                  25                  30 tgg atg aac tgg gtg aag cag agg cct gga cag ggt ctt gag tgg att        144
Trp Met Asn Trp Val Lys Gln Arg Pro Gly Gln Gly Leu Glu Trp Ile
```

```
            35                  40                  45
gga cag att tgg cct gga gat ggt gat act aac tac aat gga aag ttc    192
Gly Gln Ile Trp Pro Gly Asp Gly Asp Thr Asn Tyr Asn Gly Lys Phe
        50                  55                  60 aag ggt aaa gcc act ctg act gcc gac gaa tcc tcc agc aca gcc tac    240
Lys Gly Lys Ala Thr Leu Thr Ala Asp Glu Ser Ser Ser Thr Ala Tyr
 65                  70                  75                  80 atg caa ctc agc agc cta cga tct gag gac tct gcg gtc tat tct tgt    288
Met Gln Leu Ser Ser Leu Arg Ser Glu Asp Ser Ala Val Tyr Ser Cys
                 85                  90                  95 gca aga cgg gag act acg acg gta ggc cgt tat tac tat gct atg gac    336
Ala Arg Arg Glu Thr Thr Thr Val Gly Arg Tyr Tyr Tyr Ala Met Asp
            100                 105                 110 tac tgg ggc caa ggg acc acg gtc acc gtc tcc tca                    372
Tyr Trp Gly Gln Gly Thr Thr Val Thr Val Ser Ser
        115                 120

<210> SEQ ID NO 4
<211> LENGTH: 124
<212> TYPE: PRT
<213> ORGANISM: Artificial Sequence
<220> FEATURE:
<223> OTHER INFORMATION: Description of Artificial Sequence: Synthetic
      anti-CD19 antibody, cA19

<400> SEQUENCE: 4

Gln Val Gln Leu Gln Glu Ser Gly Ala Glu Leu Val Arg Pro Gly Ser
 1               5                  10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
 65                  70                  75                  80

Met Gln Leu Ser Ser Leu Arg Ser Glu Asp Ser Ala Val Tyr Ser Cys
                 85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 5
<211> LENGTH: 108
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ile Lys Tyr
            20                  25                  30

Leu Asn Trp Tyr Gln Gln Thr Pro Gly Lys Ala Pro Lys Leu Leu Ile
        35                  40                  45

Tyr Glu Ala Asn Ser Leu Gln Ala Gly Val Pro Ser Arg Phe Ser Gly
    50                  55                  60

Ser Gly Ser Gly Thr Asp Tyr Thr Phe Thr Ile Ser Ser Leu Gln Pro
 65                  70                  75                  80
```

```
Glu Asp Ile Ala Thr Tyr Tyr Cys Gln Gln Tyr Gln Ser Leu Pro Tyr
                85                  90                  95

Thr Phe Gly Gln Gly Thr Lys Leu Gln Ile Thr Arg
            100                 105

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Chimeric
      cA19Vk antibody

<400> SEQUENCE: 6

Asp Ile Gln Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Gln Ile Lys Arg
            100                 105                 110

<210> SEQ ID NO 7
<211> LENGTH: 112
<212> TYPE: PRT
<213> ORGANISM: Artificial Sequence
<220> FEATURE:
<223> OTHER INFORMATION: Description of Artificial Sequence: Synthetic
      humanized hA19Vk antibody

<400> SEQUENCE: 7

Asp Ile Gln Leu Thr Gln Ser Pro Ser Ser Leu Ser Ala Ser Val Gly
 1               5                  10                  15

Asp Arg Val Thr Ile Thr Cys Lys Ala Ser Gln Ser Val Asp Tyr Asp
                20                  25                  30

Gly Asp Ser Tyr Leu Asn Trp Tyr Gln Gln Ile Pro Gly Lys Ala Pro
            35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Tyr Thr Phe Thr Ile Ser
 65                  70                  75                  80

Ser Leu Gln Pro Glu Asp Ile Ala Thr Tyr His Cys Gln Gln Ser Thr
                85                  90                  95

Glu Asp Pro Trp Thr Phe Gly Gly Gly Thr Lys Leu Gln Ile Lys Arg
            100                 105                 110

<210> SEQ ID NO 8
<211> LENGTH: 117
<212> TYPE: PRT
<213> ORGANISM: Homo sapiens

<400> SEQUENCE: 8
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Trp Leu His Trp Val Arg Gln Ala Pro Gly Gln Gly Leu Glu Trp Met
        35                  40                  45

Gly Gly Ile Val Pro Met Phe Gly Pro Pro Asn Tyr Ala Gln Lys Phe
    50                  55                  60

Gln Gly Arg Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Gly Gly Tyr Gly Ile Tyr Ser Pro Glu Trp Gly Gln Gly Ser Leu
                100                 105                 110

Val Thr Val Ser Ser
            115

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Chimeric
      cA19VH antibody

<400> SEQUENCE: 9

Gln Val Gln Leu Gln Glu Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Arg Ser Glu Asp Ser Ala Val Tyr Ser Cys
                85                  90                  95

Ala Arg Arg Glu Thr Thr Thr Val Gly Arg Tyr Tyr Tyr Ala Met Asp
                100                 105                 110

Tyr Trp Gly Gln Gly Thr Thr Val Thr Val Ser Ser
            115                 120

<210> SEQ ID NO 10
<211> LENGTH: 124
<212> TYPE: PRT
<213> ORGANISM: Artificial Sequence
<220> FEATURE:
<223> OTHER INFORMATION: Description of Artificial Sequence: Synthetic
      humanized hA19VH antibody

<400> SEQUENCE: 10

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Ala Phe Ser Ser Tyr
            20                  25                  30

Trp Met Asn Trp Val Arg Gln Arg Pro Gly Gln Gly Leu Glu Trp Ile
        35                  40                  45
```

```
Gly Gln Ile Trp Pro Gly Asp Gly Asp Thr Asn Tyr Asn Gly Lys Phe
    50                  55                  60
Lys Gly Arg Ala Thr Ile Thr Ala Asp Glu Ser Thr Asn Thr Ala Tyr
 65                  70                  75                  80
Met Glu Leu Ser Ser Leu Arg Ser Glu Asp Thr Ala Phe Tyr Ser Cys
                 85                  90                  95
Ala Arg Arg Glu Thr Thr Thr Val Gly Arg Tyr Tyr Tyr Ala Met Asp
             100                 105                 110
Tyr Trp Gly Gln Gly Thr Thr Val Thr Val Ser Ser
        115                 120
```

<210> SEQ ID NO 11
<211> LENGTH: 11
<212> TYPE: PRT
<213> ORGANISM: Homo sapiens

<400> SEQUENCE: 11

```
Trp Gly Gln Gly Ser Leu Val Thr Val Ser Ser
 1               5                  10
```

<210> SEQ ID NO 12
<211> LENGTH: 336
<212> TYPE: DNA
<213> ORGANISM: Artificial Sequence
<220> FEATURE:
<223> OTHER INFORMATION: Description of Artificial Sequence: Synthetic humanized anti-CD19 antibody, hA19Vk
<220> FEATURE:
<221> NAME/KEY: CDS
<222> LOCATION: (1)..(336)

<400> SEQUENCE: 12

```
gac atc cag ctg acc cag tct cca tca tct ctg agc gca tct gtt gga         48
Asp Ile Gln Leu Thr Gln Ser Pro Ser Ser Leu Ser Ala Ser Val Gly
 1               5                  10                  15
gat agg gtc act atc act tgt aag gcc agc caa agt gtt gat tat gat         96
Asp Arg Val Thr Ile Thr Cys Lys Ala Ser Gln Ser Val Asp Tyr Asp
             20                  25                  30
ggt gat agt tat ttg aac tgg tac cag cag att cca ggg aaa gca cct        144
Gly Asp Ser Tyr Leu Asn Trp Tyr Gln Gln Ile Pro Gly Lys Ala Pro
         35                  40                  45
aaa ttg ttg atc tac gat gct tcg aat cta gtt tct ggt atc cct cct        192
Lys Leu Leu Ile Tyr Asp Ala Ser Asn Leu Val Ser Gly Ile Pro Pro
     50                  55                  60
cga ttc tct ggc agc gga tct ggg aca gat tac act ttc acc atc agc        240
Arg Phe Ser Gly Ser Gly Ser Gly Thr Asp Tyr Thr Phe Thr Ile Ser
 65                  70                  75                  80
tct ctt caa cca gaa gac att gca aca tat cac tgt cag caa agt act        288
Ser Leu Gln Pro Glu Asp Ile Ala Thr Tyr His Cys Gln Gln Ser Thr
                 85                  90                  95
gaa gat ccg tgg acg ttc ggt gga ggg acc aag cta cag atc aaa cgt        336
Glu Asp Pro Trp Thr Phe Gly Gly Gly Thr Lys Leu Gln Ile Lys Arg
            100                 105                 110
```

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic humanized anti-CD19 antibody, hA19Vk

<400> SEQUENCE: 13

```
Asp Ile Gln Leu Thr Gln Ser Pro Ser Ser Leu Ser Ala Ser Val Gly
 1               5                  10                  15

Asp Arg Val Thr Ile Thr Cys Lys Ala Ser Gln Ser Val Asp Tyr Asp
                20                  25                  30

Gly Asp Ser Tyr Leu Asn Trp Tyr Gln Gln Ile Pro Gly Lys Ala Pro
            35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Tyr Thr Phe Thr Ile Ser
 65              70                  75                  80

Ser Leu Gln Pro Glu Asp Ile Ala Thr Tyr His Cys Gln Gln Ser Thr
                85                  90                  95

Glu Asp Pro Trp Thr Phe Gly Gly Gly Thr Lys Leu Gln Ile Lys Arg
            100                 105                 110
```

<210> SEQ ID NO 14
<211> LENGTH: 372
<212> TYPE: DNA
<213> ORGANISM: Artificial Sequence
<220> FEATURE:
<223> OTHER INFORMATION: Description of Artificial Sequence: Synthetic humanized anti-CD19 antibody, hA19VH
<220> FEATURE:
<221> NAME/KEY: CDS
<222> LOCATION: (1)..(372)

<400> SEQUENCE: 14

```
cag gtc caa ctg cag caa tca ggg gct gaa gtc aag aaa cct ggg tca      48
Gln Val Gln Leu Gln Gln Ser Gly Ala Glu Val Lys Lys Pro Gly Ser
 1               5                  10                  15 tcg gtg aag gtc tcc tgc aag gct tct ggc tac gct ttc agt agc tac      96
Ser Val Lys Val Ser Cys Lys Ala Ser Gly Tyr Ala Phe Ser Ser Tyr
                20                  25                  30 tgg atg aac tgg gtg agg cag agg cct gga cag ggt ctt gag tgg att     144
Trp Met Asn Trp Val Arg Gln Arg Pro Gly Gln Gly Leu Glu Trp Ile
            35                  40                  45 gga cag att tgg cct gga gat ggt gat act aac tac aat gga aag ttc     192
Gly Gln Ile Trp Pro Gly Asp Gly Asp Thr Asn Tyr Asn Gly Lys Phe
    50                  55                  60 aag ggg cgc gcc act att act gcc gac gaa tcc act aat aca gcc tac     240
Lys Gly Arg Ala Thr Ile Thr Ala Asp Glu Ser Thr Asn Thr Ala Tyr
 65              70                  75                  80 atg gaa ctc agc agc cta cga tct gag gac aca gcg ttc tat tct tgt     288
Met Glu Leu Ser Ser Leu Arg Ser Glu Asp Thr Ala Phe Tyr Ser Cys
                85                  90                  95 gca aga cgg gag act acg acg gta ggc cgt tat tac tat gct atg gac     336
Ala Arg Arg Glu Thr Thr Thr Val Gly Arg Tyr Tyr Tyr Ala Met Asp
            100                 105                 110 tac tgg ggc caa ggg acc acg gtc acc gtc tcc tca                     372
Tyr Trp Gly Gln Gly Thr Thr Val Thr Val Ser Ser
            115                 120
```

<210> SEQ ID NO 15
<211> LENGTH: 124
<212> TYPE: PRT
<213> ORGANISM: Artificial Sequence
<220> FEATURE:
<223> OTHER INFORMATION: Description of Artificial Sequence: Synthetic humanized anti-CD19 antibody, hA19VH

<400> SEQUENCE: 15

Gln Val Gln Leu Gln Gln Ser Gly Ala Glu Val Lys Lys Pro Gly Ser

```
                1               5                  10                  15
Ser Val Lys Val Ser Cys Lys Ala Ser Gly Tyr Ala Phe Ser Ser Tyr
                    20                  25                  30

Trp Met Asn Trp Val Arg Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Arg Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Ser Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Ala Ser Gln Ser Val Asp Tyr Asp Gly Asp Ser Tyr Leu Asn
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Ala Ser Asn Leu Val Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Gln Ser Thr Glu Asp Pro Trp Thr
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Tyr Trp Met Asn
1               5
```

```
<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Ile Trp Pro Gly Asp Gly Asp Thr Asn Tyr Asn Gly Lys Phe Lys
 1               5                  10                  15
Gly

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Glu Thr Thr Thr Val Gly Arg Tyr Tyr Tyr Ala Met Asp Tyr
 1               5                  10                  15

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 22

Gly Gly Gly Ser
 1

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 23

Gly Gly Gly Gly Ser Gly Gly Gly Ser Gly Gly Gly Gly Ser
 1               5                  10                  15

<210> SEQ ID NO 24
<211> LENGTH: 126
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atcacttgta aggccagcca agtgttgat tatgatggtg atagttattt gaactggtac      60
cagcagattc cagggaaagc acctaaattg ttgatctacg atgcttcgaa tctagtttct    120
ggtatc                                                               126

<210> SEQ ID NO 25
<211> LENGTH: 125
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 25
tgctgacagt gatatgttgc aatgtcttct ggttgaagag agctgatggt gaaagtgtaa      60
tctgtcccag atccgctgcc agagaatcga ggagggatac cagaaactag attcgaagca    120
tcgta                                                                  125

<210> SEQ ID NO 26
<211> LENGTH: 86
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tccgacatcc agctgaccca gtctccatca tctctgagcg catctgttgg agatagggtc      60
actatcactt gtaaggccag ccaaag                                            86

<210> SEQ ID NO 27
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gctccttgag atctgtagct tggtccctcc accgaacgtc cacggatctt cagtactttg      60
ctgacagtga tatgttgcaa t                                                 81

<210> SEQ ID NO 28
<211> LENGTH: 137
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctggctacgc tttcagtagc tactggatga actgggtgag gcagaggcct ggacagggtc      60
ttgagtggat tggacagatt tggcctggag atggtgatac taactacaat ggaaagttca    120 agggcgcgc cactatt                                                     137

<210> SEQ ID NO 29
<211> LENGTH: 129
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgtagtctcc cgtcttgcac aagaatagaa cgctgtgtcc tcagatcgta ggctgctgag      60
ttccatgtag gctgtattag tggattcgtc ggcagtaata gtggcgcgcc ccttgaactt    120
tccattgta                                                             129

<210> SEQ ID NO 30

```
<211> LENGTH: 93
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caggtccaac tgcagcaatc aggggctgaa gtcaagaaac ctgggtcatc ggtgaaggtc      60
tcctgcaagg cttctggcta cgctttcagt agc                                  93

<210> SEQ ID NO 31
<211> LENGTH: 89
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgaggagacg gtgaccgtgg tcccttggcc ccagtagtcc atagcatagt aataacggcc     60
taccgtcgta gtctcccgtc ttgcacaag                                       89
```